(12) United States Patent
Schudok et al.

(10) Patent No.: US 7,153,876 B2
(45) Date of Patent: Dec. 26, 2006

(54) MALONAMID AND MALONAMIC ESTER DERIVATIVES WITH ANTITHROMBOTIC ACTIVITY, THEIR PREPARATION, AND THEIR USE

(75) Inventors: Manfred Schudok, Eppstein/Ts. (DE); Otmar Klingler, Rodgau (DE); Hans-Peter Nestler, Kelkheim (DE); Hans Matter, Langenselbold (DE); Herman Schreuder, Hofheim-Lorsbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 139 days.

(21) Appl. No.: 10/634,827

(22) Filed: Aug. 6, 2003

(65) Prior Publication Data

US 2004/0034027 A1 Feb. 19, 2004

Related U.S. Application Data

(62) Division of application No. 09/965,790, filed on Oct. 1, 2001, now Pat. No. 6,645,992.

(30) Foreign Application Priority Data

Sep. 30, 2000 (EP) .................................. 00121551

(51) Int. Cl.
C07D 213/75 (2006.01)
A61K 31/44 (2006.01)
A61P 7/02 (2006.01)
A61P 9/10 (2006.01)

(52) U.S. Cl. ...................... 514/345; 514/357; 546/291; 546/300

(58) Field of Classification Search ................ 546/291, 546/300; 514/345, 357
See application file for complete search history.

(56) References Cited

U.S. PATENT DOCUMENTS

2003/0027828 A1 2/2003 Schudok et al.

FOREIGN PATENT DOCUMENTS

| WO | 97/48706 A | 12/1997 |
| WO | 97/49684 A | 12/1997 |
| WO | 00/01704 A | 1/2000 |

OTHER PUBLICATIONS

H. Cole, "The tissue factor pathway of coagulation," *Aust. J. Med. Sci.*, 16:87-93 (1995).
G. J. Broze, Jr., "Tissue factor pathway inhibitor and the current concept of blood coagulation," *Blood Coagulation and Fibrinolysis*, 6(Suppl. 1):S7-S13 (1995).
L. A. Harker et al., "Antithrombotic and Antilesion Benefits without Hemorrhagic Risks by Inhibiting Tissue Factor Pathway," *Haemostasis*, 26 (Suppl. 1):76-82 (1996).
L. A. Harker et al., "Antithrombotic Benefits and Hemorrhagic Risks of Direct Thrombin Antagonists," *Thrombosis and Haemostasis*, 74(1):464-472 (1995).
Y. Cheng and W. H. Prusoff, "Relationship Between the Inhibition Constant ($K_1$) and the Concentration of Inhibitor Which Causes 50 Per Cent Inhibition ($I_{50}$) of an Enzymatic Reaction," *Biochem. Pharmacol.*, 22:3099-3108 (1973).
I. H. Segel, Enzyme Kinetics: Behavior And Analysis Of Rapid Equilibrium And Steady-State Enzyme Systems 100-125 (John Wiley & Sons, New York 1975).
J. A. Ostrem et al., "Discovery of a Novel, Potent, and Specific Family of Factor Xa Inhibitors via Combinatorial Chemistry," *Biochemistry*, 37:1053-1059 (1998).
J. E. Hall et al., "Anti-*Pneumocystis* Activities of Aromatic Diamidoxime Prodrugs," *Antimicrobial Agents and Chemotherapy*, 42(3):666-674 (1998).
G. E. Davies and J. S. Lowe, "The Inhibition of Guinea-Pig Plasma Kallikrein by Amidines," *Advances in Experimental Medicine and Biology*, 8:453-460 (1970).
International Search Report for International Application No. PCT/EP 01/10845 (Nov. 27, 2001).
Geratz et al., "Diamidino-α,ω-diphenoxyalkanes. Structure-Activity Relationships for the Inhibition of Thrombin, Pancreatic Kallikrein, and Trypsin," *Journal of Medicinal Chemistry* 16(9):970-975 (1973).
Rauch et al., "Thrombus formation on atherosclerotic plaques: pathogenesis and clinical consequences," *Ann. Intern. Med.*, 134(3):224-238 (2001).
Van Aken et al., "Anticoagulation: the present and future," *Clin. Appl. Thromb. Hemost.*, 7(3):195-204 (2001).

Primary Examiner—Venkataraman Balasubramanian
(74) Attorney, Agent, or Firm—Ronald G. Ort

(57) ABSTRACT

Compounds of formula I,

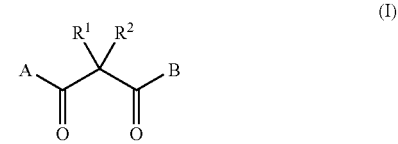

(I)

in which $R^1$, $R^2$, A, and B having the definitions set forth in the claims, are valuable pharmacologically active compounds, which exhibit a strong antithrombotic effect and are suitable, for example, for treating thromboembolic diseases and restenoses. They are reversible inhibitors of the blood clotting enzyme factor VIIa and can in general be applied in conditions in which an undesired activity of factor VIIa is present or for the cure or prevention of which an inhibition of factor VIIa is intended. Also disclosed are processes for the preparation of compounds of formula I, their use, in particular as active ingredients in pharmaceuticals, and pharmaceutical preparations comprising them.

6 Claims, No Drawings

MALONAMID AND MALONAMIC ESTER DERIVATIVES WITH ANTITHROMBOTIC ACTIVITY, THEIR PREPARATION, AND THEIR USE

This application is a divisional application of U.S. patent application Ser. No. 09/965,790, filed Oct. 1, 2001, now U.S. Pat. No. 6,645,992, the entirety of which is incorporated herein by reference.

The present invention relates to compounds of formula I,

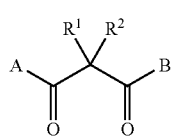

in which $R^1$, $R^2$, A, and B have the meanings indicated below.

Compounds of formula I are valuable as pharmacologically active compounds. They exhibit a strong antithrombotic effect and are suitable, for example, for the therapy and prophylaxis of thromboembolic diseases and restenoses. They are inhibitors of the blood clotting enzymes, including factor VIIa, and can in general be applied in conditions in which an undesired activity of factor VIIa is present or for the cure, treatment, or prevention of which an inhibition of factor VIIa is intended. The invention further relates to processes for the preparation of compounds of formula I, their use, for example, as active ingredients in pharmaceuticals, and pharmaceutical preparations comprising them.

Normal haemostasis is the result of a complex balance between the processes of clot initiation, formation, and clot dissolution. The complex interactions between blood cells, specific plasma proteins, and the vascular surface, maintain the fluidity of blood unless injury and blood loss occurs.

Many significant disease states are related to abnormal haemostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation.

The ability to form blood clots is vital to survival. The formation of a blood clot or a thrombus is normally the result of tissue injury which initiates the coagulation cascade and has the effect of slowing or preventing blood flow in wound healing. Other factors which are not directly related to tissue injury like atherosclerosis and inflammation may also initiate the coagulation cascade. In general, a relationship exists between inflammation and the coagulation cascade. Inflammation mediators regulate the coagulation cascade and coagulation components influence the production and activity of inflammation mediators. However, in cenain disease states the formation of blood clots within the circulatory system reaches an undesirable level and is itself the source of morbidity potentially leading to pathological consequences. It is nevertheless not desirable in such disease states to completely inhibit the blood clotting system because life threatening hemorrhage would ensue. In the treatment of such states, a well-balanced intervention into the blood clotting system is required.

Blood coagulation is a complex process involving a progressively amplified series of enzyme activation reactions in which plasma zymogens are sequentially activated by limited proteolysis. Mechanistically, the blood coagulation cascade has been divided into intrinsic and extrinsic pathways, which converge at the activation of factor X. Subsequent generation of thrombin proceeds through a single common pathway (see Scheme 1 below). Present evidence suggests that the intrinsic pathway plays an important role in the maintenance and growth of fibrin formation, while the extrinsic pathway is critical in the initiation phase of blood coagulation (H. Cole, Aust. J. Med. Sci. 16 (1995) 87; G. J. Broze, Blood Coagulation and Fibrinolysis 6, Suppl. 1 (1995) S7). It is generally accepted that blood coagulation is physically initiated upon formation of a factor VIIa/tissue factor (TF) complex. Once formed, this complex rapidly initiates coagulation by activating factors IX and X. The newly generated activated factor X, i.e., factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/TF complex (extrinsic pathway) is suppressed by a Kunitz-type protease inhibitor protein, TFPI, which, when complexed to factor Xa, can directly inhibit the proteolytic activity of factor VIIa/TF.

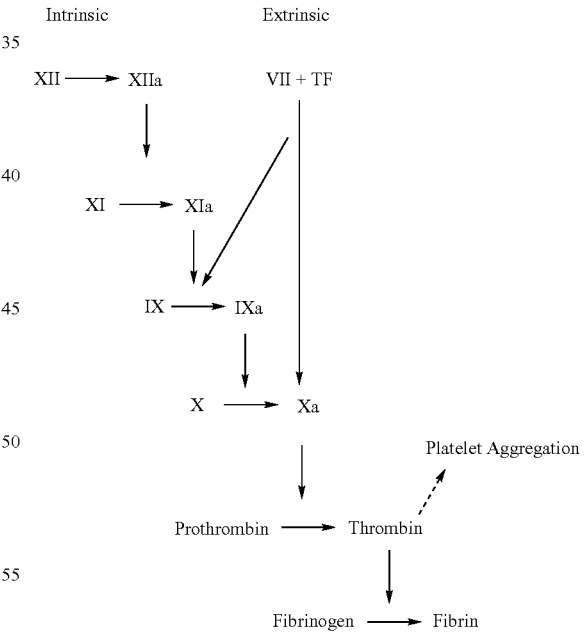

Scheme 1: Blood coagulation cascade

In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin. The autocatalytic nature of thrombin generation is an important safeguard against uncontrolled bleeding and it ensures that, once a given threshold level of prothrombinase is present, blood coagulation will proceed to completion. Thus, it is most desirable to develop agents that inhibit coagulation without directly inhibiting thrombin but by inhibiting other steps in the coagulation cascade like factor VIIa activity.

In many clinical applications, there is a great need for the prevention of intravascular blood clots or for some anticoagulant treatment. For example, nearly 50% of patients who have undergone a total hip replacement develop deep vein thrombosis ("DVT"). The currently available drugs, like heparin and derivatives thereof, are not satisfactory in many specific clinical applications. The currently approved therapies include fixed dose low molecular weight heparin ("LMWH") and variable dose heparin. Even with these drug regimes, 10% to 20% of patients develop DVT, and 5% to 10% develop bleeding complications.

Another exemplary clinical situation for which better anticoagulants are needed concerns subjects undergoing transluminal coronary angioplasty and subjects at risk for myocardial infarction or suffering from crescendo angina. The present, conventionally accepted therapy, which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The widely used blood-clotting inhibitors like heparin and related sulfated polysaccharides like LMWH and heparin sulfate exert their anticlotting effects by promoting the binding of a natural regulator of the clotting process, antithrombin III, to thrombin and to factor Xa. The inhibitory activity of heparin primarily is directed toward thrombin, which is inactivated approximately 100 times faster than factor Xa. Hirudin and hirulog are two additional thrombin-specific anticoagulants presently in clinical trials. However, these anticoagulants which inhibit thrombin also are associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors (L. A. Harker et al., Thromb. Hemostas. 74 (1995) 464).

Specific inhibition of the factor VIIa/TF catalytic complex using monoclonal antibodies (WO-A-92/06711) or a protein such as chloromethyl ketone inactivated factor VIIa (WO-A-96/12800 and WO-A-97/47651) is an extremely effective means of controlling thrombus formation caused by acute arterial injury or the thrombotic complications related to bacterial septicemia. There is also experimental evidence suggesting that inhibition of factor VIIa/TF activity inhibits restenoses following balloon angioplasty (L. A. Harker et al., Haemostasis 26 (1996) S1:76). Bleeding studies have been conducted in baboons and indicate that inhibition of the factor VIIa/TF complex has the widest safety window with respect to therapeutic effectiveness and bleeding risk of any anticoagulant approach tested including thrombin, platelet, and factor Xa inhibition (L. A. Harker et al., Thromb. Hemostas. 74 (1995) 464).

A specific inhibitor of factor VIIa which has a favorable property profile would have substantial practical value in the practice of medicine. In particular, a factor VIIa inhibitor would be effective under circumstances where the present drugs of choice, like heparin and related sulfated polysaccharides, are ineffective or only marginally effective. Certain inhibitors of factor VIIa have already been described. EP-A-987274, for example, discloses compounds containing a tripeptide unit which inhibit factor VIIa. However, the property profile of these compounds is still not ideal, and there is a need for further low molecular weight factor VIIa-specific blood clotting inhibitors that are effective and do not cause unwanted side effects. The present invention satisfies this need by providing novel factor VIIa activity malonicacid derivatives of formula I.

Thus, embodiments of the present invention are compounds of formula I,

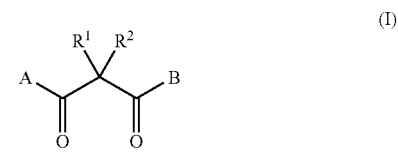

wherein:

A is a derivative of formula II,

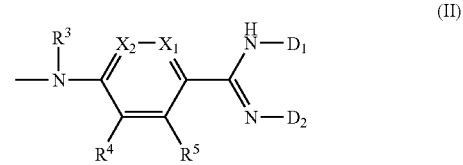

wherein:

$R^3$ is hydrogen, —OH, or —($C_1$–$C_7$)-alkyl;

$R^4$ and $R^5$, independently of one another, are
1. hydrogen;
2. —($C_1$–$C_7$)-alkyl;
3. —OH;
4. —O—($C_1$–$C_7$)-alkyl;
5. halogen;
6. —$NH_2$; or
7. —$NO_2$;

$X_1$ and $X_2$, independently of one another, are selected from a carbon substituted by $R^4$, wherein $R^4$ is as defined above, and a nitrogen;

$D_1$ and $D_2$, independently of one another, are
1. hydrogen;
2. —C(O)—($C_1$–$C_7$)-alkyl;
3. —C(O)-aryl;
4. —C(O)—($C_1$–$C_7$)-alkyl-aryl;
5. —C(O)—O—($C_1$–$C_7$)-alkyl;
6. —C(O)—O—($C_1$–$C_7$)-alkyl-aryl; or
7. —C(O)—O—($C_1$–$C_6$)-aryl; or $D_1$ is hydrogen, when $D_2$ is
1. —OH;
2. —O—C(O)—($C_1$–$C_7$)-alkyl;
3. —O—C(O)-aryl; or
4. —O—C(O)—($C_1$–$C_7$)-alkyl-aryl; or $D_1$ and $D_2$, together with the nitrogen to which they are attached, form a cycle of formula VIII

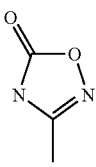

(VIII)

R¹ is 1. hydrogen;
2. —($C_1$–$C_7$)-alkyl;
3. —OH;
4. —O—($C_1$–$C_7$)-alkyl; or
5. —N—($R^6$)$_2$, wherein $R^6$ is, independently of one another, hydrogen, —C(O)-aryl, —C(O)—($C_1$–$C_7$)-alkyl-aryl, —C(O)—($C_1$–$C_7$)-alkyl, —($C_1$–$C_7$)-alkyl, —C(O)—N(H)-aryl, —C(O)—N(H)—($C_1$–$C_7$)-alkyl-aryl, —($C_1$–$C_6$)—N(H)-alkyl, —C(O)—O-aryl, —C(O)—O—($C_1$–$C_7$)-alkyl-aryl, —C(O)—O—($C_1$–$C_7$)-alkyl-, S(O$_2$)-aryl, or —S(O$_2$)—($C_1$–$C_7$)-alkyl;
R² is 1. aryl, wherein aryl is unsubstituted or mono- to tri-substituted, independently of one another, by
1.1 —CF$_3$;
1.2 halogen;
1.3 —OH;
1.4 —CN;
1.5 sulfo;
1.6 —NO$_2$;
1.7 —NH$_2$;
1.8 —O—($C_1$–$C_7$)-alkyl;
1.9 substituted amino;
1.10 —COOH;
1.11 —($C_1$–$C_7$)-alkyl;
1.12 carbamyl;
1.13 carbonyl;
1.14 alkoxycarbonyl;
1.15 methylendioxyl;
1.16 aryloxy, wherein aryloxy is unsubstituted or mono- to tri-substituted, independently of one another, by a substituent as defined by 1.1 to 1.15;
1.17 —O—($C_1$–$C_7$)-alkyl-aryl, wherein aryl is unsubstituted or mono- to tri-substituted, independently of one another, by a substituent as defined by 1.1 to 1.15;
1.18 Het-group, wherein Het-group is unsubstituted or mono- to tri-substituted, independently of one another, by a substituent as defined by 1.1 to 1.15; or
1.19 —($C_0$–$C_4$)-alkyl-aryl, wherein aryl is unsubstituted or mono- to tri-substituted, independently of one another, by a substituent as defined by 1.1 to 1.15;
2. hydrogen;
3. Het-group, wherein Het-group is unsubstituted or mono- to tri-substituted, independently of one another, by a substituent as defined by 1.1 to 1.19 above;
4. —(CH$_2$)$_m$—Y$_n$—(CH$_2$)$_o$-aryl, in which
m, n, and o are, independently of one another, 0, 1, or 2, provided that at least one of m, n, and o is not 0;
aryl is unsubstituted or mono- to tri-substituted, independently of one another, by a substituent as defined by 1.1 to 1.19 above; and
Y is —O—, —S—, or —N—($R^6$) wherein $R^6$ is hydrogen or —($C_1$–$C_7$)-alkyl, provided n is 1, or Y is —N($R^6$)—N($R^6$)— wherein $R^6$ is, independently of one another, hydrogen or —($C_1$–$C_7$)-alkyl, or —N=N—, provided n is 2; or 5. —(CH$_2$)$_m$—Y$_n$—(CH$_2$)$_o$-Het-group, in which
m, n, and o are, independently of one another, 0, 1, or 2, provided that at least one of m, n, and o is not 0;
Het-group is unsubstituted or mono- to tri-substituted, independently of one another, by a substituent as defined by 1.1 to 1.19 above; and
Y is as defined above; or
R¹ and R², together with the carbon to which they are bonded, form
1. a —($C_3$–$C_7$)-cycloalkyl, wherein cycloalkyl is unsubstituted or mono- to tri-substituted, independent of one another, by a substituent as defined by 1.1 to 1.19 above;
2. a —($C_3$–$C_7$)-cycloalkyl, wherein cycloalkyl is unsubstituted or mono- to disubstituted, independently of one another, and fused to an aryl- or Het-group-ring, which itself is unsubstituted or mono- to tri-substituted, independently of one another, by a substituent as defined by 1.1 to 1.19 above;
3. a Het-group, wherein the Het-group is unsubstituted or mono- to tri-substituted, independently of one another, by a substituent as defined by 1.1 to 1.19 above; or
4. a keto-group, which may partially or totally exist in a hydrated state;

provided that, when R¹ is as defined above under 3, 4, or 5, then R² is not directly bonded to formula I via a oxygen-, sulfur-, or nitrogen-;
B is 1. —N($R^7$)—(CH—($R^8$))$_p$-aryl, in which
aryl is unsubstituted or mono- to tri-substituted, independently of one another, by a substituent as defined by 1.1 to 1.19 above;
p is 0, 1, or 2;
$R^7$ is 1.1 hydrogen;
1.2 —($C_1$–$C_7$)-alkyl;
1.3 —OH; or
1.4 —N—($R^6$)$_2$, wherein $R^6$ is, independently of one another, hydrogen or —($C_1$–$C_7$)-alkyl;
$R^8$ is 1.1 hydrogen;
1.2 —($C_1$–$C_7$)-alkyl;
1.3 —($C_2$–$C_7$)-alkenyl;
1.4 —($C_2$–$C_7$)-alkynyl;
1.5 —(($C_0$–$C_3$)-alkyl-($C_3$–$C_7$)-cycloalkyl;
1.6 —CN;
1.7 aryl, aryl is unsubstituted or mono- or di-substituted, independently of one another, by a substituent as defined by 1.1 to 1.19 above;
1.8 a Het-group, wherein the Het-group is unsubstituted or mono- or di-substituted, independently of one another, by a substituent as defined by 1.1 to 1.19 above;
1.9 —(CH—($R^8$))— forms a —($C_3$–$C_7$)-cycloalkyl derivative; or
1.10 —(($C_0$–$C_4$)-alkyl-O—($C_1$–$C_7$)-alkyl;
2. —O—(CH—($R^8$))$_p$-aryl, wherein aryl, $R^8$, and p are as defined above;
3. —N($R^7$)—(CH—($R^8$))$_p$-Het-group, wherein the Het-group is unsubstituted or mono- or di-substituted, independently of one another, by a substituent as defined by 1.1 to 1.19 above, and $R^7$, $R^8$, and p are as defined above;
4. —N($R^9$)—N($R^{9'}$)—(CH—($R^8$))$_q$-aryl, in which
aryl is unsubstituted or mono- to tri-substituted, independently of one another, by a substituent as defined by 1.1 to 1.19 above;
q is 0, 1, or 2;
$R^9$ and $R^{9'}$ are, independently of one another, hydrogen, —($C_1$–$C_7$)-alkyl, or —($C_1$–$C_3$)-alkyl-aryl; and $R^8$ is as defined above;

5. —O—N($R^9$)—(CH—($R^8$))$_q$-aryl, in which
   aryl is unsubstituted or mono- to tri-substituted, independently of one another, by a substituent as defined by 1.1 to 1.19 above;
   q is 0, 1, or 2; and
   $R^8$ and $R^9$ are as defined above;
6. —N($R^9$)—N($R^{9'}$)—(CH—($R^8$))$_q$-Het-group, in which
   Het-group is unsubstituted or mono- to tri-substituted, independently of one another, by a substituent as defined by 1.1 to 1.19 above;
   q is 0, 1, or 2; and
   $R^8$, $R^{9'}$, and $R^9$ are as defined above; or
7. —O—N($R^9$)—(CH—($R^8$))$_q$-Het-group, in which
   Het-group is unsubstituted or mono- to tri-substituted, independently of one another, by a substituent as defined by 1.1 to 1.19 above;
   q is 0, 1, or 2; and
   $R^8$ and $R^9$ are as defined above;

in any stereoisomeric form or mixture thereof in any ratio, or a physiologically tolerable salt thereof.

Other embodiments of the invention are compounds of formula I, wherein
A is a derivative of formula II, wherein
  $R^3$ is hydrogen;
  $R^4$ and $R^5$, independently of one another, are hydrogen or halogen; and
  $X_1$ and $X_2$, independently of one another, are carbon or nitrogen;
$R^1$ is hydrogen or —($C_1$–$C_2$)-alkyl;
$R^2$ is hydrogen, phenyl, or —($C_1$–$C_2$)-alkyl-phenyl;
B is 1. —N($R^7$)—(CH—($R^8$))$_p$-aryl, in which
  aryl is indanyl, phenyl, tetralinyl, naphthalinyl, which are unsubstituted or mono- to di-substituted, independently of one another, by
    1.1 Br, Cl, or F;
    1.2 —$CF_3$;
    1.3 —$NO_2$;
    1.4 methylendioxyl;
    1.5 —OH;
    1.6 phenyl;
    1.7 phenoxy;
    1.8 benzyloxy;
    1.9 —O—($C_1$–$C_7$)-alkyl-phenyl, wherein phenyl is unsubstituted or mono- to tri-substituted, independently of one another, by
      1.9.1 Br, Cl, or F;
      1.9.2 —($C_1$–$C_4$)-alkyl; or
      1.9.3 —$NO_2$;
    1.10 —C(O)—O—($C_1$–$C_4$)-alkyl;
    1.11 —O—($C_1$–$C_4$-)-alkyl;
    1.12 —$SO_2$—($C_1$–$C_4$)-alkyl;
    1.13 —COOH;
    1.14 —($C_1$–$C_3$)-alkyl; or
    1.15 methoxyl;
  p is 0, 1, or 2;
  $R^7$ is hydrogen;
  $R^8$ is 1.1 hydrogen;
    1.2 —($C_1$–$C_2$)-alkyl;
    1.3 —CN;
    1.4 phenyl, wherein phenyl is unsubstituted or mono- or di-substituted, independently of one another, by methoxy or halogen;
    1.5 —($C_0$–$C_2$)-alkyl-O—($C_1$–$C_4$)-alkyl;
    1.6 —(CH—($R^8$))— forms a —($C_4$–$C_6$)-cycloalkyl derivative;
    1.7 cyclopropylmethyl; or
    1.8 ethynyl;
2. —O—(CH—($R^8$))$_p$-phenyl, wherein phenyl, $R^8$, and p are as defined above;
3. —N($R^9$)—N($R^{9'}$)—(CH—($R^8$))$_q$-Het-group, in which
   Het-group is quinoxaline, imidazolyl, benzimidazolyl, oxazolyl, benzoxazolyl, thiazolyl, indazolyl, benzothiazolyl, indolyl, indolinyl, or pyridinyl, wherein Het-group is unsubstituted or mono- to di-substituted, independently of one another, by
     1.1 Br, Cl, or F;
     1.2 —$CF_3$;
     1.3 —$NO_2$;
     1.4 methylendioxyl;
     1.5 —OH;
     1.6 phenyl;
     1.7 phenoxy;
     1.8 benzyloxy;
     1.9 —O—($C_1$–$C_7$)-alkyl-phenyl, wherein phenyl is unsubstituted or mono- to tri-substituted, independently of one another, by
       1.9.1 Br, Cl, or F;
       1.9.2 —($C_1$–$C_4$)-alkyl; or
       1.9.3 —$NO_2$;
     1.10 —C(O)—O—($C_1$–$C_4$)-alkyl;
     1.11 —O—($C_1$–$C_4$)-alkyl;
     1.12 —$SO_2$—($C_1$–$C_4$)-alkyl;
     1.13 —COOH;
     1.14 —($C_1$–$C_3$)-alkyl; or
     1.15 methoxyl;
   $R^9$ and $R^{9'}$ are, independently of one another, hydrogen or —($C_1$–$C_2$)-alkyl;
   $R^8$ is 1.1 hydrogen;
     1.2 —($C_1$–$C_2$)-alkyl;
     1.3 —CN;
     1.4 phenyl, wherein phenyl is unsubstituted or mono- or di-substituted, independently of one another, by methoxy or halogen;
     1.5 —($C_0$–$C_2$)-alkyl-O—($C_1$–$C_4$)-alkyl;
     1.6 —(CH—($R^8$))— forms a —($C_4$–$C_6$)-cycloalkyl derivative;
     1.7 cyclopropylmethyl; or
     1.8 ethynyl; and
   q is 0, 1, or 2; or
4. —N($R^7$)—(CH—($R^8$))$_p$-Het-group$^2$, wherein
   Het-group$^2$ is imidazolyl, benzimidazolyl, oxazolyl, benzoxazolyl, thiazolyl, benzothiazolyl, indolyl, indazolyl, indolinyl, or pyridinyl, wherein Het-group$^2$ is unsubstituted or mono-substituted by Br, Cl, F, —$CF_3$, —$NO_2$, phenyl, phenoxy, methyl, benzyloxy, or methoxy;
   p is 0, 1, or 2;
   $R^7$ is hydrogen;
   $R^8$ is 1.1 hydrogen;
     1.2 —($C_1$–$C_2$)-alkyl;
     1.3 —CN;
     1.4 phenyl, wherein phenyl is unsubstituted or mono- or di-substituted, independently of one another, by methoxy or halogen;
     1.5 —($C_0$–$C_2$)-alkyl-O—($C_1$–$C_4$)-alkyl;
     1.6 —(CH—($R^8$))— forms a —($C_4$–$C_6$)-cycloalkyl derivative;
     1.7 cyclopropylmethyl; or
     1.8 ethynyl.

As used herein, the term "alkyl" is to be understood in the broadest sense to mean hydrocarbon derivatives which can be linear, i.e., straight-chain, or branched, and can be acyclic or cyclic groups or comprise any combination of acyclic and cyclic subunits. Further, the term alkyl as used herein expressly includes saturated groups as well as unsaturated groups which latter groups contain one or more (for example, one, two, or three) double bonds and/or triple bonds, provided that the double bonds are not located within a cyclic alkyl group in such a manner that an aromatic system results. All these statements also apply if an alkyl group carries substituents or occurs as a substituent on another group, for example, in an alkoxy group (alkyl-O—), an alkoxycarbonyl group, or an arylalkyl group.

Examples of alkyl groups containing 1, 2, 3, 4, 5, 6, or 7 carbon atoms are methyl, ethyl, propyl, butyl, pentyl, hexyl, or heptyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl, or tert-pentyl. It should be understood that while specific examples of embodiments within the scope of the invention are defined for illustrative purposes, it is not the intent to limit the claims to those examples unless it is specifically so stated in this specification or the subsequently prepared prosecution history.

Unsaturated alkyl groups are, for example, alkenyl groups such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl groups such as ethynyl, 1-propynyl, 2-propynyl (=propargyl), or 2-butynyl. Alkyl groups can also be unsaturated when they are substituted. The fact that the specification and the appended claims specifically indicate that certain groups of formula I can optionally be substituted or unsubstituted (e.g., aryl and Het-group) and set forth numerous specific possible substitutions, does not mean that the other groups of formula I (e.g., alkyl, alkyl-aryl, alkenyl, and cycloalkyl) can not also be substituted. In other words, the use of the phrase "unsubstituted and substituted" to modify one group of formula I in the specification and claims should not be used to construe that other groups cannot be substituted, absent an explicit statement in the specification.

Examples of cyclic alkyl groups are cycloalkyl groups containing 3, 4, 5, 6, or 7 ring carbon atoms like cyclopropyl, cyclobutyl, cyclopentyl, cyclohexyl, or cycloheptyl, which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, 1-cyclopropylethyl-, 1-cyclobutylethyl-, 1-cyclopentylethyl-, 2-cyclopropylethyl-, 2-cyclobutylethyl-, 2-cyclopentylethyl-, 3-cyclopropylpropyl-, or 3-cyclobutylpropyl-, in which groups the cycloalkyl subgroup as well as acyclic subgroup can also be unsaturated and/or substituted.

A cyclic alkyl group has to contain at least three carbon atoms, and an unsaturated alkyl group has to contain at least two carbon atoms. Thus, a group like $(C_1-C_7)$-alkyl is to be understood as comprising, among others, saturated acyclic $(C_1-C_7)$-alkyl, $(C_3-C_7)$-cycloalkyl, cycloalkyl-alkyl groups like $(C_3-C_7)$-cycloalkyl-$(C_1-C_3)$-alkyl- wherein the total number of carbon atoms can range from 4 to 7, and unsaturated $(C_2-C_7)$-alkyl, like $(C_2-C_7)$-alkenyl or $(C_2-C_7)$-alkynyl. Similarly, a group like $(C_1-C_4)$-alkyl is to be understood as comprising, among others, saturated acyclic $(C_1-C_4)$-alkyl, $(C_3-C_4)$-cycloalkyl, cyclopropyl-methyl-, and unsaturated $(C_2-C_4)$-alkyl, like $(C_2-C_4)$-alkenyl or $(C_2-C_4)$-alkynyl.

The term "aryl" refers to a monocyclic or polycyclic hydrocarbon derivative in which at least one carbocyclic ring is present that has a conjugated pi electron system. In a $(C_6-C_{14})$-aryl group, from 6 to 14 ring carbon atoms are present. Examples of $(C_6-C_{14})$-aryl groups are phenyl, naphthyl, indanyl, tetralinyl, biphenylyl, fluorenyl, or anthracenyl. Examples of $(C_6-C_{10})$-aryl groups are phenyl or naphthyl. Unless stated otherwise, and irrespective of any specific substituents bonded to aryl groups which are indicated in the definition of compounds of formula I, aryl groups, for example, phenyl, naphthyl, or fluorenyl, can in general be unsubstituted or substituted by one or more, for example, one, two, or three, identical or different substituents. Aryl groups can be bonded via any desired position, and in substituted aryl groups, the substituents can be located in any desired position.

In monosubstituted phenyl groups, the substituent can be located in the 2-position, the 3-position, or the 4-position, usually the 3-position and the 4-position. If a phenyl group carries two substituents, they can be located in 2,3-position, 2,4-position, 2,5-position, 2,6-position, 3,4-position, or 3,5-position. In phenyl groups carrying three substituents, the substituents can be located in 2,3,4-position, 2,3,5-position, 2,3,6-position, 2,4,5-position, 2,4,6-position, or 3,4,5-position. Naphthyl groups can be 1-naphthyl and 2-naphthyl. In substituted naphthyl groups, the substituents can be located in any position, for example, in monosubstituted 1-naphthyl groups, in the 2-, 3-, 4-, 5-, 6-, 7-, or 8-position, and in monosubstituted 2-naphthyl groups, in the 1-, 3-, 4-, 5-, 6-, 7-, or 8-position. Biphenylyl groups can be biphenyl-2-yl, biphenyl-3-yl, or biphenyl4-yl. Fluorenyl groups can be bonded via the 1-, 2-, 3-, 4-, or 9-position. In monosubstituted fluorenyl groups bonded via the 9-position, the substituent is preferably present in the 1-, 2-, 3-, or 4-position.

The above statements relating to aryl groups correspondingly apply to divalent groups derived from aryl groups, i.e., to arylene groups like phenylene which can be unsubstituted or substituted 1,2-phenylene, 1,3-phenylene, or 1,4-phenylene, or naphthylene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl. The above statements also correspondingly apply to the aryl subgroup in arylalkyl- groups. Examples of arylalkyl- groups which can also be unsubstituted or substituted in the aryl subgroup, as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl. All the above explanations also correspondingly apply to aromatic rings which may be condensed (or fused) to a ring formed by the groups $R^1$ and $R^2$ and the carbon atom to which these groups are attached. These examples are illustrative but not all encompassing, and there is no intention to be limited to just these.

The "Het-group" or "Het-group$^2$" (collectively, "Het-group") comprises groups containing 3, 4, 5, 6, 7, 8, 9, or 10 ring atoms in the parent monocyclic or bicyclic heterocyclic ring system. In monocyclic Het-groups, the heterocyclic ring preferably is a 3-membered, 4-membered, 5-membered, 6-membered, or 7-membered ring, usually a 5-membered or 6-membered ring. In bicyclic Het-groups, usually two fused rings are present, one of which is a 5-membered ring or 6-membered heterocyclic ring, and the other of which is a 5-membered or 6-membered heterocyclic or carbocyclic ring, i.e., a bicyclic ring Het-group typically contains 8, 9, or 10 ring atoms, usually 9 or 10 ring atoms.

Het-group comprises saturated heterocyclic ring systems which do not contain any double bonds within the rings, as well as unsaturated heterocyclic ring systems, including mono-unsaturated and poly-unsaturated heterocyclic ring systems which contain one or more, for example, one, two, three, four, or five, double bonds within the rings, provided that the resulting system is stable. Unsaturated rings may be partially unsaturated or non-aromatic, or they may be aromatic, i.e., double bonds within the rings in the Het-group may be arranged in such a manner that a conjugated pi electron system results. Aromatic rings in a Het-group may be 5-membered or 6-membered rings, i.e., aromatic groups in a Het-group contain 5 to 10 ring atoms. Aromatic rings in a Het group thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a Het-group, one or both rings may contain heteroatoms. Aromatic Het-groups may also be referred to by the customary term heteroaryl for which all the definitions and explanations above and below relating to Het-group correspondingly apply. These explanations relating to the saturation/unsaturation in heterocyclic ring systems representing the Het-group correspondingly apply to any other heterocyclic ring system that can be present in a compound of formula I, for example, to a ring formed by $R^1$ and $R^2$, together with the carbon to which these groups are bonded, and the ring systems that may be condensed to this ring.

In a Het-group and any other heterocyclic group, 1 or 2 identical or different ring heteroatoms may be selected from nitrogen, oxygen, and sulfur atoms are present. In general, the ring heteroatoms can be present in any desired combination and in any desired positions with respect to each other provided that the resulting heterocyclic system is known in the art and is stable and suitable as a subgroup in a drug substance. Examples of parent structures of heterocycles from which the Het-group can be derived are aziridine, oxirane, azetidine, pyrrole, furan, thiophene, dioxole, imidazole, pyrazole, oxazole, isoxazole, thiazole, isothiazole, thiadiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, or pyridopyrimidines, as well as ring systems which result from the listed heterocycles by fusion (or condensation) of a carbocyclic ring, for example, benzo-fused, cyclopenta-fused, cyclohexa-fused, or cyclohepta-fused derivatives of these heterocycles.

The fact that many of the before-listed names of heterocycles are the chemical names of unsaturated or aromatic ring systems does not imply that the Het-groups and other heterocyclic groups could only be derived from the respective unsaturated ring system. The names here only serve to describe the ring system with respect to ring size and the number of the heteroatoms and their relative positions and are exemplary. As explained above, for each exemplary example, a Het-group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which a Het-group and any other heterocyclic group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), 2,3-dihydrobenzo[1,4]dioxine, 3,4-dihydro-2H-benzo[1,4]oxazine, perhydro-1,4-thiazine (=thiomorpholine), perhydroazepine, indoline, isoindoline, 1,2,3,4-tetrahydroquinoline, or 1,2,3,4-tetrahydroisoquinoline.

The Het-group and any other heterocyclic group may be bonded via any ring carbon atom, and in the case of nitrogen heterocycles, via any suitable ring nitrogen atom, if applicable. Thus, for example, a pyrrolyl group can be pyrrol-1-yl, pyrrol-2-yl, or pyrrol-3-yl, a pyrrolidinyl group can be pyrrolidin-1-yl (=pyrrolidino), pyrrolidin-2-yl, or pyrrolidin-3-yl, a pyridinyl group can be pyridin-2-yl, pyridin-3-yl, or pyridin-4-yl, and a piperidinyl group can be piperidin-1-yl (=piperidino), piperidin-2-yl, piperidin-3-yl, or piperidin-3-yl. Furyl can be furan-2-yl or fur-3-yl, thienyl can be thiophen-2-yl or thiophen-3-yl, imidazolyl can be imidazol-1-yl, imidazol-2-yl, imidazol-4-yl, or imidazol-5-yl, 1,3-oxazolyl can be 1,3-oxazol-2-yl, 1,3-oxazol-4-yl, or 1,3-oxazol-5-yl, 1,3-thiazolyl can be 1,3-thiazol-2-yl, 1,3-thiazol-4-yl, or 1,3-thiazol-5-yl, pyrimidinyl can be pyrimidin-2-yl, pyrimidin-4-yl (=pyrimidin-6-yl), or pyrimidin-5-yl, and piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl, or indol-7-yl. Similarly, benzimidazolyl, benzoxazolyl, and benzothiazol groups can be bonded via the 2-position and via any of the positions 4, 5, 6, and 7. Quinolinyl can be quinolin-2-yl, quinolin-3-yl, quinolin-4-yl, quinolin-5-yl, quinolin-5-yl, quinolin-7-yl, or quinolin-8-yl, and isoqinolinyl can be isoquinolin-1-yl, isoquinolin-3-yl, isoquinolin-4-yl, isoquinolin-5-yl, isoquinolin-6-yl, isoquinolin-7-yl, or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

The term "substituted amino" refers to $N(R^{10})_x$, where $R^{10}$ is an alkyl or aryl, and x is 1 or 2. The term "sulfo" refers to $S(O)_yR^{11}$, where $R^{11}$ is an alkyl, aryl, amino, or substituted amino, and y is 0, 1, or 2. The term "halogen" is understood as meaning fluorine, chlorine, bromine, or iodine. The term "—$(C_0–C_4)$-alkyl-aryl" is understood as meaning an aryl, which is substituted by no —$CH_2$— derivative in the case of $C_o$-alkyl, —$CH_2$— derivative in the case of $C_1$-alkyl, —$CH_2$—$CH_2$— derivative in the case of $C_2$-alkyl, —$CH_2$—$CH_2$—$CH_2$— derivative in the case of $C_3$-alkyl, and —$CH_2$—$CH_2$—$CH_2$—$CH_2$— derivative in the case of $C_4$-alkyl.

Optically active carbon atoms present in compounds of formula I can, independently of each other, have R configuration or S configuration. Compounds of formula I can be present in the form of pure enantiomers or pure diastereomers or in the form of mixtures of enantiomers and/or diastereomers, for example, in the form of racemates. The present invention relates to pure enantiomers and mixtures of enantiomers as well as to pure diastereomers and mixtures of diastereomers. The invention comprises mixtures of two or more than two stereoisomers of formula I, and it comprises any ratio of the stereoisomers in the mixtures. Compounds of formula I can be present as E isomers or Z isomers (or cis isomers or trans isomers) and the invention relates both to pure E isomers and pure Z isomers and to E/Z mixtures in any ratio. The invention also comprises all tautomeric forms of compounds of formula I.

Diastereomers, including E/Z isomers, can be separated into the individual isomers, for example, by chromatography. Racemates can be separated into the two enantiomers by customary methods, for example, by chromatography on chiral phases or by resolution, for example, by crystallization of diastereomeric salts obtained with optically active acids or bases. Stereochemically uniform compounds of formula I can also be obtained by employing stereochemically uniform starting materials or by using stereoselective reactions.

"Physiologically tolerable salts" of compounds of formula I are nontoxic salts that are physiologically acceptable, in particular pharmaceutically utilizable salts. Such salts of compounds of formula I containing acidic groups, for example, a carboxy group COOH, are, for example, alkali metal salts or alkaline earth metal salts such as sodium salts, potassium salts, magnesium salts, and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine, or tris-(2-hydroxyethyl)-amine. Basic groups contained in compounds of formula I, for example, amino groups or amidino groups, form acid addition salts, for example, with inorganic acids such as hydrochloric acid, hydrobromic acid, sulfuric acid, nitric acid, or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid, or p-toluenesulfonic acid. The present invention also includes acid addition salts of compounds of formula I which contain, for example, two basic groups, with one or two acid equivalents.

Salts of compounds of formula I can be obtained by customary methods known to those skilled in the art, for example, by combining a compound of formula I with an inorganic or organic acid or base in a solvent or diluent, or from other salts by cation exchange or anion exchange. Embodiments of the present invention also includes all salts of compounds of formula I which, because of low physiologically tolerability, are not directly suitable for use in pharmaceuticals but are suitable, for example, as intermediates for carrying out further chemical modifications of compounds of formula I or as starting materials for the preparation of physiologically tolerable salts.

The anions of the mentioned acids that may be present in acid addition salts of compounds of formula I, are also examples of anions that may be present in compounds of formula I if they contain one or more positively charged groups like trialkylammonio-substituents, i.e., groups of the formula (alkyl)$_3$N$^+$ bonded via the positively charged nitrogen atom, representing R$^{10}$, or quaternized ring nitrogen atoms in heterocyclic groups. In general, a compound of formula I contains one or more physiologically tolerable anions or anion equivalents as counterions if it contains one or more permanently positively charged groups like trialkylammonio. Compounds of formula I which simultaneously contain a basic group or a positively charged group and an acidic group, for example, an amidino group and a carboxy group, can also be present as zwitterions (betaines) which are likewise included in the present invention.

Certain embodiments of the present invention furthermore include all solvates of compounds of formula I, for example, hydrates or adducts with alcohols. The invention also includes derivatives and modifications of compounds of formula I, for example, prodrugs, protected forms, and other physiologically tolerable derivatives, including esters and amides of acid groups, as well as active metabolites of compounds of formula I.

Embodiments of the present invention also relate to processes of preparation by which compounds of formula I are obtainable. Compounds of formula I can generally be prepared by linkage of two or more fragments (or building blocks) which can be derived retrosynthetically from formula I. In preparing compounds of formula I, it can generally be advantageous or necessary in the course of the synthesis to introduce functional groups which could lead to undesired reactions or side reactions in a synthesis step in the form of precursors which are later converted into the desired functional groups. As examples of precursor groups, cyano groups may be mentioned, which may later be converted into amidino groups, or nitro groups, which may be converted into amino groups. Protecting groups (or blocking groups) that may be present on functional groups include allyl, tert-butyl, benzyl, allyloxycarbonyl (Alloc), tert-butoxycarbonyl (Boc), benzyloxycarbonyl (Z), and 9-fluorenylmethoxycarbonyl (Fmoc) as protecting groups for hydroxy, carboxylic acid, amino, and amidino groups.

In particular, in the preparation of compounds of formula I, building blocks can be connected by performing one or more condensation reactions and/or addition reactions such as amide couplings, i.e., by forming an amide bond between a carboxylic acid group of one building block and an amino group of another building block. For example, compounds of formula I can be prepared by linking the building blocks of formulae III, IV, and V

(III)

(IV)

(V)

wherein R$^{10}$ and R$^{11}$ are, independently of each other, a —OH group, an acid chloride, an ester like a (C$_1$–C$_4$)-alkyl ester or an activated ester, or a mixed anhydride, or any other activated species resulting from the reaction of the carboxylic acid with coupling reagents, and R$^1$, R$^2$, R$^3$, R$^4$, R$^5$, R$^7$, R$^8$, X$_1$, X$_2$, B, p, and aryl are as defined for formula I, by means of forming in a manner known per se an amide bond between the carboxylic acid derivative depicted in formula III and the NHR$^3$ group depicted in formula IV and an amide bond or ester bond between the carboxylic acid derivative depicted in formula III and the —OH— or —NH-group depicted in formula V.

The starting compounds of formulae III, IV, and V, and other compounds which are employed in the synthesis of compounds of formula I for introducing certain structural units, are commercially available or can be readily prepared from commercially available compounds or by analogous procedures described below or in the literature, which is readily available to those skilled in the art.

For the preparation of compounds of formula I, compounds of formulae III and IV may be linked and the resulting intermediate product then condensed with a compound of formula V to give a compound of formula I. Also, compounds of formulae III and V may be condensed and the resulting intermediate product then linked to a compound of formula IV to give a compound of formula I. After any such reaction step in the course of such syntheses, protecting and deprotecting steps and conversions of precursor groups into the desired final groups may be carried out and further modifications may be made.

Various general methods for the formation of an amide bond that can be employed in the synthesis of compounds of formula I are well known to those skilled in the art, for example, from peptide chemistry. An amide coupling step can favorably be carried out by employing a free carboxylic acid, i.e., a compound of formula III, activating that carboxylic acid group, e.g., in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano(ethoxycarbonyl)methylene)amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound of formula IV. An amide bond can also be formed by reacting an amino compound with a carboxylic acid halide, usually, a carboxylic acid chloride, which can be prepared in a separate step or in situ from a carboxylic acid and, for example, thionyl chloride, or a carboxylic acid ester or thioester, for example, a methyl ester, ethyl ester, phenyl ester, nitrophenyl ester, pentafluorophenyl ester, methylthio ester, phenylthio ester, or pyridin-2-ylthio ester, i.e., with a compound of formula III.

The activation reactions and coupling reactions are usually performed in the presence of an inert solvent (or diluent), for example, in the presence of an aprotic solvent like dimethylformamide (DMF), tetrahydrofuran (THF), dichloromethane (DCM), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also, depending on the specific process, it may be necessary or advantageous to add in a suitable amount one or more auxiliary agents, for example, a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or a N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, *Advanced Organic Chemistry*, 4th ed., John Wiley & Sons, 1992; or Houben-Weyl, *Methoden der organischen Chemie* [Methods of Organic Chemistry], Georg Thieme Verlag.

Protective groups that may still be present in the products obtained in the coupling reaction are then removed by standard procedures. For example, tert-butyl protecting groups, in particular, a tert-butoxycarbonyl group which is a protected form of an amidino group, can be deprotected, i.e., converted into the amidino group, by treatment with trifluoroacetic acid. Also, as already explained, after the coupling reaction, functional groups can be generated from suitable precursor groups. In addition, a conversion into a physiologically tolerable salt or a prodrug of a compound of formula I can then be carried out by known processes.

In general, a reaction mixture containing a final compound of formula I or an intermediate is worked up and, if desired, the product is then purified by customary processes known to those skilled in the art. For example, a synthesized compound can be purified using well known methods such as crystallization, chromatography, or reverse phase-high performance liquid chromatography (RP-HPLC) or other methods of separation based, for example, on the size, charge, or hydrophobicity of the compound. Similarly, well known methods such as amino acid sequence analysis, NMR, IR, and mass spectrometry (MS) can be used for characterizing a compound of the invention.

Compounds of formula I, which on account of its chemical structure occurs in enantiomeric forms, can be resolved into the substantially pure enantiomers by salt formation with enantiomerically pure acids or bases, chromatography on chiral stationary phases, or derivatization by means of chiral enantiomerically pure compounds such as amino acids, separation of the diastereomers thus obtained, and removal of the chiral auxiliary groups.

Compounds of formula I can be isolated either in free form or, in the case of the presence of acidic or basic groups, converting it into physiologically tolerable salts. The preparation of physiologically tolerable salts of compounds of formula I capable of salt formation, including their stereoisomeric forms, is carried out in a manner known per se. With basic reagents such as hydroxides, carbonates, hydrogencarbonates, alkoxides, and also ammonia or organic bases, for example, trimethyl- or triethylamine, ethanolamine or triethanolamine, or alternatively basic amino acids, for example, lysine, ornithine, or arginine, the carboxylic acids form stable alkali metal, alkaline earth metal, or optionally substituted ammonium salts. If compounds of formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic, or trifluoroacetic acid are suitable.

Compounds of formula I can be prepared by starting from malonic acid diesters, compounds of formula III, wherein $R^{10}$ and $R^{11}$ are identical or different, usually methyl, ethyl, benzyl, or t-butyl. The selective cleavage of one ester group can be accomplished by applying the appropriate method, as described, e.g., in T. W. Greene and P. G. M. Wuts, *Protective Groups in Organic Synthesis*, 3$^{rd}$ ed., Wiley, New York, 1999. The protective groups, for example, methyl, ethyl, or benzyl, can be cleaved by, for example, 1 eq. of KOH in Ethanol and subsequent acidification and extraction. As an alternative, suitable protected derivatives or precursors of the amidines of derivative A can be used, for example, the cyanides, hydroxyamidines, or other.

Compounds of formula I can also be prepared by starting from malonic acids, compounds of formula III, wherein $R^{10}$ and $R^{11}$ are both hydrogen atoms. The free malonic diacids can be transformed to a salt, e.g., the DIPEA- or triethylamine salt by using one equivalent of an appropriate base, and then transformed to a mono acid chloride with, e.g., thionyl chloride or other related reagents. This acid chloride will then be reacted with an amine (B), or, e.g., the amidino aniline (A) or the respective derivative or precursor, e.g., cyanide. The second component to complete the synthesis, can then be introduced, followed, if necessary, by transformation of the amidine and/or one or more deprotection steps. Alternatively, it is also possible, to use standard coupling procedures for the synthesis of the mono-amide from the diacid, but separation from remaining diacid and symmetrical diamide is then often necessary.

Compounds of formula I can also be prepared by starting from phenyl acetic acids or related substituted acetic acids or their esters When $R^1$ is hydrogen and $R^2$ is, e.g., aryl, such as phenyl, it is possible to apply the well-known carboxylation reaction for the synthesis of malonic acid derivatives, resulting in malonic acid diesters (depending on the starting compounds used: mixed or non-mixed) or mono esters. As a starting material, e.g., a (substituted) phenyl acetic acid ester (methyl, ethyl, t-butyl preferred), has to be first deprotonated by using BuLi, phenolate, LDA, $NaNH_2$, NaH, or other related strong bases followed by $CO_2$ or $CO_2$-equivalents like diethylcarbonate or chloroformates.

Therefore, it is possible to synthesize mono-esters if $CO_2$ is used in this reaction circumventing single ester cleavage or mixed diesters if, e.g., diethylcarbonate is used together with a different ester group of the phenyl acetate.

Starting material, such as those described above, can be modified to result in diamides within the scope of the invention through the following processes: B: Malonic acid ester amides (this comprises all compounds containing an amidino bearing group A connected to the parents malonate via the amide bond and an ester moiety —C(=O)—O— as part of B in the general formula I, e.g., malonamic esters)

1. Starting with Malonic Acid Diesters or the thus Resulting Mono Esters:

For the introduction of the desired derivative as part of B., it is possible (a) to esterify an appropriate monoester of the starting malonate and then, after selective cleavage of the protective second ester, to couple the amidine or amidine equivalent/precursor as described above.

(b) Alternatively, it is also possible, first, to couple the amine of the amidino-containing derivative resulting in the malonamic ester, then to cleave the protective ester group and esterify with the desired alcohol, followed by deprotection steps, if necessary.

2. Starting from Malonic Acids:

By using the above mentioned method, it is also possible, to esterify the acid chloride with an alcohol of component B (which is present in the final product), followed by introduction of the amidine containing group or amidine precursor A.

3. Starting from Phenyl Acetic Acids or Related Substituted Acetic Acids or their Esters:

The carboxylation reaction can be performed in the same manner as described above, typically using benzyl- or t-butyl-esters of the starting side chain containing acid. If a second ester-group was introduced in the carboxylation reaction, first, selective cleavage of one ester should be accomplished, then esterification with the desired alcohol as part of B, present in the final product. After second selective cleavage of the remaining ester protective group, coupling with the amidine- or amidine precursor containing derivative has to be done, eventually followed by deprotection step(s).

Alternatively, the order of introduction of both derivatives can be changed, as described above for the diamide synthesis. Another possibility is the introduction of the finally present ester group as part of B in general formula I into, e.g., phenyl acetic acid or the related starting acid, followed then by the carboxylation reaction and the coupling of the amidine or amidine precursor, if necessary, after cleavage of the protective second ester and followed by deprotection/transformation of the amidine precursor.

Amidine and Amidine Precursors:

At least two different principle ways for the introduction of the amidine containing moiety A in general formula I are possible:

1. Introduction is possible by separate building block synthesis or using commercially available compounds, yet containing the amidine, and using this building block in the coupling reaction. Optionally, the amidine can be protected using standard procedures for protective group introduction.

2. Amidine precursors are usually the corresponding nitriles. So for synthetic reasons it might be advisable to do the transformation to the amidine in any later stage of the synthesis or, often more convenient, even on the last stage, therefore, eventually circumventing problems during synthesis.

Several methods for the transformation of the cyanide to the amidine are known. The method used depends on the specific chemistry of the transformation and the potential interactions with functionalities and other problems with the target molecule. Useful in the present case is the pinner reaction or the nucleophilic addition of hydroxylamine to the nitrile, followed by hydrogenation or the hydroxyamidine. If the latter method is used, it is also possible to use the intermediate hydroxyamidine in, e.g., coupling reactions, doing the hydrogenation on a latter stage or the last stage of the synthesis.

Amidines and Hydroxyamidines Might also be Used in a Protected State:

Amidines and hydroxyamidines can be modified by special derivatives which will function as prodrugs or as protective groups during synthesis.

Known groups of that kind are typically derivatives of carboxylic acids and carbamic acids like phenoxycarbonyl, benzyloxycarbonyl, 4-methoxybenzyloxycarbonyl, methoxycarbonyl, ethoxycarbonyl, benzoyl, or acetyl.

Chirality of Starting Materials—Amines or Alcohols to be Coupled to the Malonate, Containing Asymmetric Centers, can be Used in Chiral, Racemic, or any other Stereoisomeric Form, Including all Kinds of Mixtures:

Embodiments of the invention also include pharmaceuticals which comprise an efficacious amount of at least one compound of formula I and/or of a physiologically tolerable salt of compounds of formula I and/or an optionally stereoisomeric form of compounds of formula I, together with a pharmaceutically suitable and physiologically tolerable excipient, additive, and/or other active compounds and auxiliaries.

Compounds of the present invention inhibit the activity of the blood coagulation enzyme factor VIIa either directly, within the prothrombinase complex, or as a soluble subunit, or indirectly, by inhibiting the assembly of factor VIIa into the prothrombinase complex.

Because of their factor VIIa inhibitory activity, compounds of formula I are useful pharmacologically active compounds which are suitable, for example, for influencing blood coagulation (or blood clotting) and fibrinolysis, and for the treatment, including cure, therapy, and prophylaxis, of diseases such as, for example, cardiovascular disorders, thromboembolic diseases, or restenoses. Compounds of formula I and their physiologically tolerable salts and their prodrugs can be administered to animals, e.g., to mammals, including humans, as pharmaceuticals for treatment. Treatment includes cure, therapy, and prophylaxis. They can be administered on their own, or in mixtures with one another, or in the form of pharmaceutical preparations which permit enteral or parenteral administration and which contain, as active constituent, an effective amount of at least one compound of formula I and/or its physiologically tolerable salts and/or its prodrugs and a pharmaceutically acceptable carrier.

Embodiments of the present invention therefore also include compounds of formula I and/or their physiologically tolerable salts and/or their prodrugs for use as pharmaceuticals (or medicaments), to the use of compounds of formula I and/or their physiologically tolerable salts and/or their prodrugs for the production of pharmaceuticals for inhibition of factor VIIa, or for influencing blood coagulation or fibrinolysis, or for the treatment, including cure, therapy, and prophylaxis, of the diseases mentioned above or below, for example, for the production of pharmaceuticals for the treatment of cardiovascular disorders, thromboembolic diseases, or restenoses. Other embodiments of the invention relate to the use of compounds of formula I and/or their physiologically tolerable salts and/or their prodrugs for the inhibition of factor VIIa, or for influencing blood coagulation or fibrinolysis, or for the treatment of the diseases mentioned above or below, for example, for use in the treatment, including cure, therapy, and prophylaxis, of cardiovascular disorders, thromboembolic diseases, or restenoses, and to methods of treatment aimed at such purposes, including methods for said cures, therapies, and prophylaxes. Certain embodiments of the present invention furthermore relate to pharmaceutical preparations (or pharmaceutical compositions) which contain an effective amount of at least one compound of formula I and/or its physiologically tolerable salts and/or its prodrugs and a pharmaceutically acceptable carrier, i.e., one or more pharmaceutically acceptable carrier substances (or vehicles) and/or additives (or excipients).

The pharmaceuticals can be administered orally, for example, in the form of pills, tablets, lacquered tablets, coated tablets, granules, hard and soft gelatin capsules, solutions, syrups, emulsions, suspensions, or aerosol mixtures. Administration, however, can also be carried out rectally, for example, in the form of suppositories, or parenterally, for example, intravenously, intramuscularly, or subcutaneously, in the form of injection solutions or infusion solutions, microcapsules, implants, or rods, or percutaneously or topically, for example, in the form of ointments, solutions, or tinctures, or in other ways, for example, in the form of aerosols or nasal sprays.

The pharmaceutical preparations according to the invention are prepared in a manner known per se and familiar to one skilled in the art. Pharmaceutically acceptable inert inorganic and/or organic carrier substances and/or additives can be used in addition to compound(s) of formula I and/or its (their) physiologically tolerable salts and/or its (their) prodrugs. For the production of pills, tablets, coated tablets, and hard gelatin capsules it is possible to use, for example, lactose, corn starch, or derivatives thereof, talc, stearic acid, or its salts. Carrier substances for soft gelatin capsules and suppositories are, for example, fats, waxes, semisolid and liquid polyols, and natural or hardened oils. Suitable carrier substances for the production of solutions, for example, injection solutions, or of emulsions or syrups are, for example, water, saline, alcohols, glycerol, polyols, sucrose, invert sugar, glucose, and vegetable oils. Suitable carrier substances for microcapsules, implants, or rods are, for example, copolymers of glycolic acid and lactic acid. The pharmaceutical preparations normally contain about 0.5 to about 90% by weight of compounds of formula I and/or their physiologically tolerable salts and/or their prodrugs. The amount of active ingredient of formula I and/or its physiologically tolerable salts and/or its prodrugs in the pharmaceutical preparations normally is from about 0.5 to about 1000 mg, usually from about 1 to about 500 mg.

In addition to active ingredients of formula I and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents, or antioxidants. They can also contain two or more compounds of formula I and/or their physiologically tolerable salts and/or their prodrugs. In case a pharmaceutical preparation contains two or more compounds of formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in compounds of formula I allows a great deal of control over the biological and physico-chemical properties of the compounds and thus allows the selection of such desired compounds. Furthermore, in addition to at least one compound of formula I and/or its physiologically tolerable salts and/or its prodrugs, the pharmaceutical preparations can also contain one or more other therapeutically or prophylactically active ingredients.

As inhibitors of factor VIIa, compounds of formula I and their physiologically tolerable salts and their prodrugs are generally suitable for the therapy and prophylaxis of conditions in which the activity of factor VIIa plays a role or has an undesired extent, or which can favorably be influenced by inhibiting factor VIIa or decreasing its activity, or for the prevention, alleviation, or cure of which an inhibition of factor VIIa or a decrease in its activity is desired by the physician. As inhibition of factor VIIa influences blood coagulation and fibrinolysis, compounds of formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation, or cure of which a decreased activity of the blood coagulation system is desired by the physician. Certain embodiments of the present invention thus reduce or inhibit unwanted blood clotting, in particular, in an individual, by administering an effective amount of compound I or a physiologically tolerable salt or a prodrug thereof, as well as pharmaceutical preparations therefor.

Conditions in which a compound of formula I and/or a physiologically tolerable salt thereof and/or a prodrug thereof can be favorably used include, for example, cardiovascular disorders, thromboembolic diseases, or complications associated, for example, with infection or surgery. Compounds of the present invention can also be used to reduce an inflammatory response. Examples of specific disorders for the treatment, including therapy and prophylaxis, of which compounds of formula I can be used are coronary heart disease, myocardial infarction, angina pectoris, vascular restenosis, for example, restenoses following angioplasty like PTCA, adult respiratory distress syndrome, multi-organ failure, stroke, and disseminated intravascular clotting disorder. Examples of related complications associated with surgery are thromboses, like deep vein and proximal vein thrombosis, which can occur following surgery. In view of their pharmacological activity, compounds of the invention can replace other anticoagulant agents such as heparin. The use of a compound of the invention can result, for example, in a cost saving as compared to other anticoagulants.

When using compounds of formula I, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated, or whether prophylaxis is carried out. An appropriate dosage can be established using clinical approaches well known in the medical art. In general, the daily dose for achieving the desired results in an adult weighing about 75 kg is from about 0.01 to about 100 mg/kg, typically from about 0.1 to about 50 mg/kg, more typical, from about 0.1 to about 10 mg/kg, (in each case in mg per kg of body weight). The daily dose can be divided, in particular, in the case of the administration of relatively large amounts, into several, for example 2, 3, or 4, part administrations. As usual, depending on individual behavior it may be necessary to deviate upwards or downwards from the daily dose indicated.

A compound of formula I can also advantageously be used as an anticoagulant outside an individual. For example, an effective amount of a compound of the invention can be contacted with a freshly drawn blood sample to prevent coagulation of the blood sample. Further, a compound of formula I and its salts can be used for diagnostic purposes, for example, in in vitro diagnoses, and as an auxiliary or tool in biochemical investigations. For example, a compound of formula I can be used in an assay to identify the presence of factor VIIa or to isolate factor VIIa in a substantially purified form. A compound of the invention can be labeled with, for example, a radioisotope, and the labeled compound bound to factor VIIa is then detected using a routine method useful for detecting the particular label. Thus, a compound of formula I, or a salt thereof, can be used advantageously as a probe to detect the location or amount of factor VIIa activity in vivo, in vitro, or ex vivo.

Furthermore, compounds of formula I can be used as synthesis intermediates for the preparation of other compounds, in particular, of other pharmaceutically active ingredients, which are obtainable from compounds of formula I, for example, by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

Abbreviations:

| | |
|---|---|
| Boc | tert-butyl oxycarbonyl |
| DIPEA | diisopropyl-ethylamine |
| DMF | N,N-dimethylformamide |
| DMSO | dimethylsulfoxide |
| NEM | N-ethylmorpholine |
| NEt$_3$ | triethylamine |
| rt | room temperature |
| THF | tetrahydrofuran |
| TOTU | O-(cyano(ethoxycarbonyl)methyleneamino)-1,1,3,3-tetramethyluronium tetrafluoroborate |
| Z | benzyl oxycarbonyl |

When in the final step of the synthesis of a compound an acid such as trifluoroacetic acid or acetic acid is used (for example, when trifluoroacetic acid is employed to remove a tert-butyl group or when a compound is purified by chromatography using an eluent which contained such an acid) in some cases, depending on the work-up procedure, for example, the details of a freeze-drying process, the compound obtained was partially or completely in the form of a salt of the acid used, for example, in the form of the acetic acid salt or trifluoroacetic acid salt.

Example 1

N-(4-Carbamimidoyl-Phenyl)-2-Phenyl-Malonamic Acid Benzyl Ester 10 g (37 mmol) phenyl malonic acid monobenzyl ester and 7.7 g (37 mmol) 4-amidino aniline hydrochloride were dissolved in 60 ml DMF and cooled to 0° C. 12.2 g (37 mmol) TOTU and 19 ml (111 mmol) DIPEA were added and the mixture stirred at rt overnight. The solvent was removed, the residue taken up in ethyl acetate, and extracted with 10% sodium carbonate solution and brine. After drying over sodium sulfate, the solution was evaporated to dryness and extracted with diethyl ether twice. The remaining solid product was sufficiently pure.

Yield: 9.7 g ESI-MS (M+H): 388.10

Example 2

N-(4-Carbamimidoyl-Phenyl)-2-Phenyl-Malonamic Acid Sodium Salt 8.26 g (19.5 mmol) of the benzyl ester from example 1 were dissolved in 100 ml THF and stirred overnight with 20 ml 2 M aqueous NaOH. The solvent was removed after filtration, water was added, and the solution extracted with diethyl ether. The aqueous phase was freeze dried and sufficiently pure for further derivatization.

Yield: 2.6 g ESI-MS (M+H): 298.10

Example 3

N-(4-Carbamimidoyl-Phenyl)-N'-[1-(4-Nitro-Phenyl)-Ethyl]-2-Phenyl-Malonamide, Formiate 75 mg (0.235 mmol) of the sodium salt from example 2 were dissolved in 2.5 ml DMF. 85 mg (0.265 mmol) TOTU in 2.5 ml DMF were added and stirred for 30 min at rt. Then 34 μl (0.265 mmol) NEM and 53.7 mg (0.265 mmol) of (S)-1-(4-nitrophenyl)-ethylamine in 0.5 ml of DMF was added and the mixture stirred at rt overnight. After filtration, the filtrate was evaporated to dryness and purified by prep. RP-HPLC.

Yield: 12 mg ESI-MS(M+H): 446.17

Analogously to the above examples the following example compounds were prepared. The examples in Table 1 show the structures of the prepared compounds.

TABLE 1

| Example No. | Structure | Empirical Formula | Molecular Weight | ESI-MS (M + H) |
|---|---|---|---|---|
| 4 | (structure shown) | $C_{25}H_{24}N_4O_2 \cdot CH_2O_2$ | 458.5154 | 412.19 |
| 5 | (structure shown) | $C_{25}H_{25}ClN_4O_2 \cdot CH_2O_2$ | 494.9763 | 448.17 |

TABLE 1-continued

| Example No. | Structure | Empirical Formula | Molecular Weight | ESI-MS (M + H) |
|---|---|---|---|---|
| 6 | 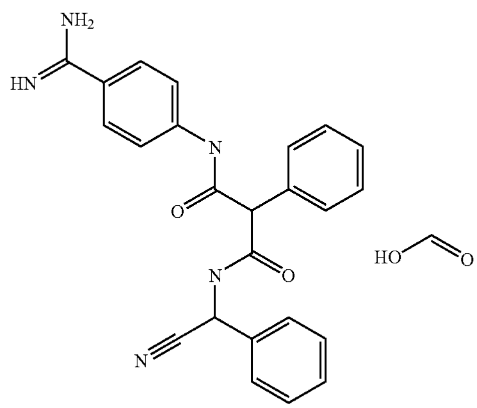 | $C_{24}H_{21}N_5O_2 \cdot CH_2O_2$ | 457.4877 | 411.17 |
| 7 | 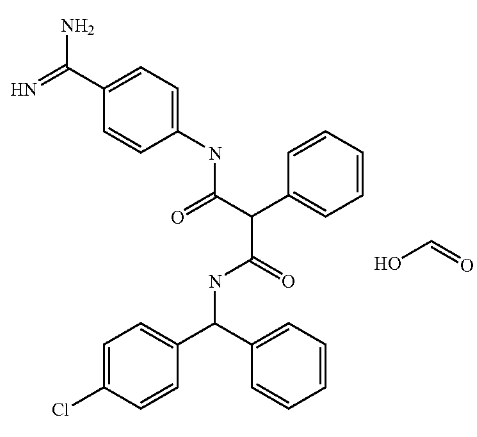 | $C_{29}H_{25}ClN_4O_2 \cdot CH_2O_2$ | 543.0203 | 496.17 |
| 8 | Chiral | $C_{27}H_{28}N_4O_3 \cdot CH_2O_2$ | 502.568 | 456.22 |

TABLE 1-continued

| Example No. | Structure | | Empirical Formula | Molecular Weight | ESI-MS (M + H) |
|---|---|---|---|---|---|
| 9 | 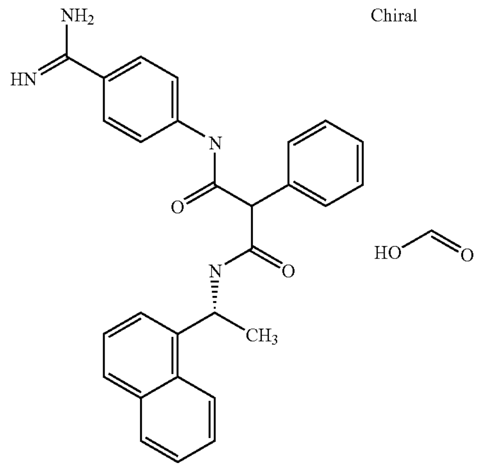 | Chiral | C₂₈H₂₆N₄O₂·CH₂O₂ | 496.5642 | 450.21 |
| 10 | 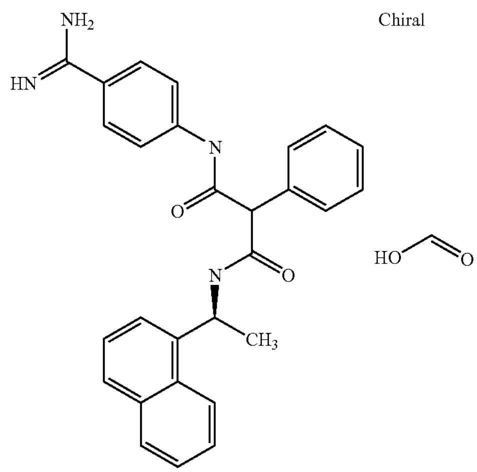 | Chiral | C₂₈H₂₆N₄O₂·CH₂O₂ | 496.5642 | 450.21 |
| 11 | 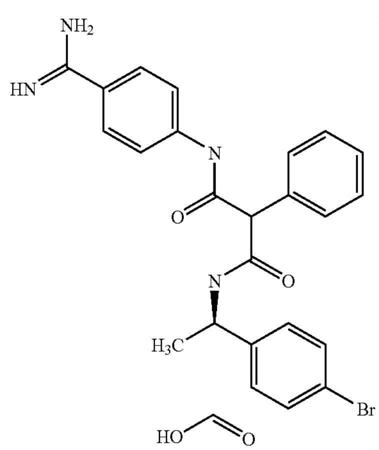 | Chiral | C₂₄H₂₃BrN₄O₂·CH₂O₂ | 525.4005 | 478.1 |

TABLE 1-continued

| Example No. | Structure | | Empirical Formula | Molecular Weight | ESI-MS (M + H) |
|---|---|---|---|---|---|
| 12 | (structure) | Chiral | $C_{24}H_{23}BrN_4O_2 \cdot CH_2O_2$ | 525.4005 | 478.1 |
| 13 | (structure) | Chiral | $C_{24}H_{23}N_5O_4 \cdot CH_2O_2$ | 491.5015 | 445.17 |
| 14 | (structure) | Chiral | $C_{28}H_{26}N_4O_2 \cdot CH_2O_2$ | 496.5642 | 450.21 |

TABLE 1-continued
| Example No. | Structure | Empirical Formula | Molecular Weight | ESI-MS (M + H) |
|---|---|---|---|---|
| 15 | 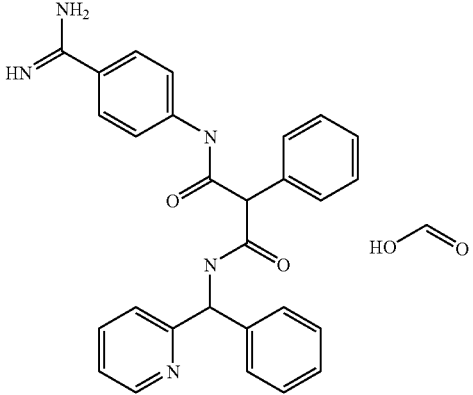 | $C_{28}H_{25}N_5O_2 \cdot CH_2O_2$ | 509.5633 | 463.2 |
| 16 | 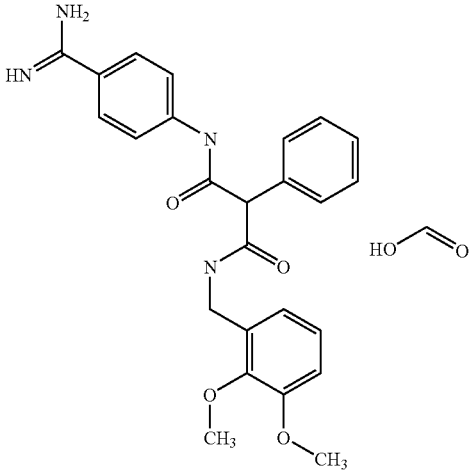 | $C_{25}H_{26}N_4O_4 \cdot CH_2O_2$ | 492.5292 | 446.2 |
| 17 | 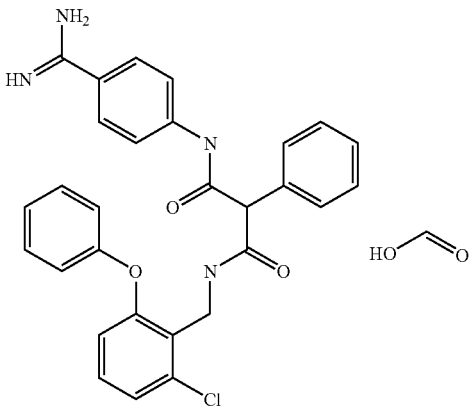 | $C_{29}H_{25}ClN_4O_3 \cdot CH_2O_2$ | 559.0193 | 512.16 |

TABLE 1-continued
| Example No. | Structure | Empirical Formula | Molecular Weight | ESI-MS (M + H) |
|---|---|---|---|---|
| 18 | 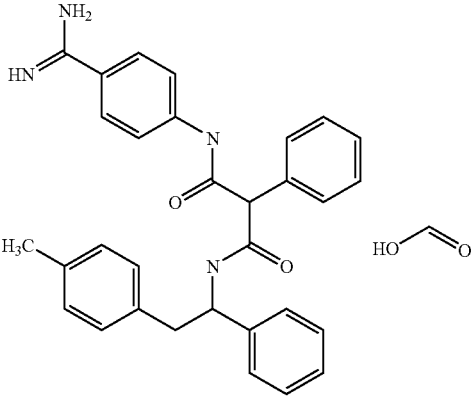 | $C_{31}H_{30}N_4O_2 \cdot CH_2O_2$ | 536.6288 | 490.24 |
| 19 | 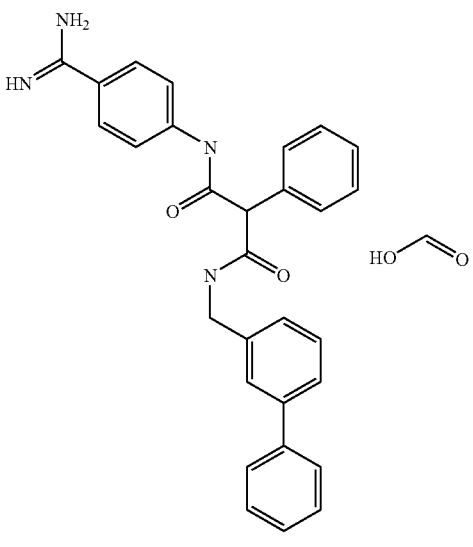 | $C_{29}H_{26}N_4O_2 \cdot CH_2O_2$ | 508.5752 | 462.21 |
| 20 | | $C_{29}H_{26}N_4O_2 \cdot CH_2O_2$ | 508.5752 | 462.21 |
| 21 | 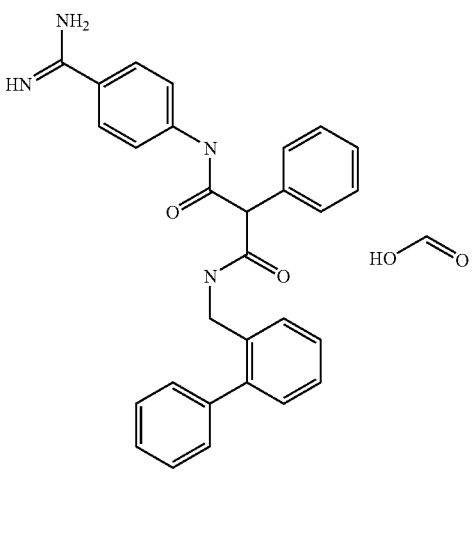 | $C_{29}H_{26}N_4O_2 \cdot CH_2O_2$ | 508.5752 | 462.21 |

TABLE 1-continued
| Example No. | Structure | Empirical Formula | Molecular Weight | ESI-MS (M + H) |
|---|---|---|---|---|
| 22 | 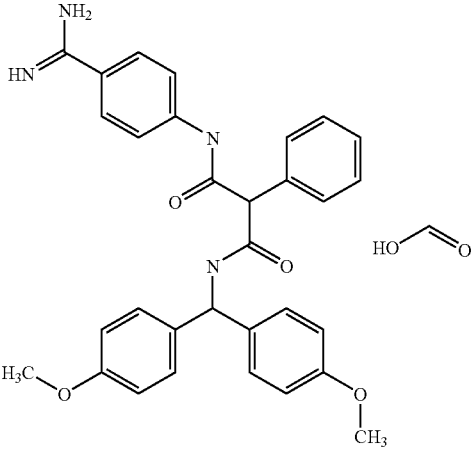 | $C_{31}H_{30}N_4O_4 \cdot CH_2O_2$ | 568.6268 | 522.23 |
| 23 | 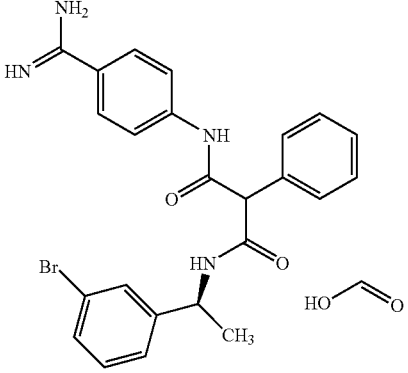 | $C_{24}H_{23}BrN_4O_2 \cdot CH_2O_2$ | 525.4005 | 478.1 |
| 24 | Chiral 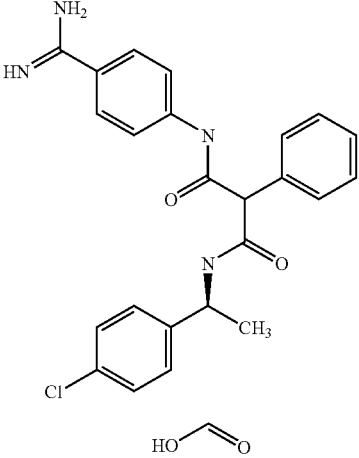 | $C_{24}H_{23}ClN_4O_2 \cdot CH_2O_2$ | 480.9495 | 434.15 |

TABLE 1-continued

| Example No. | Structure | Empirical Formula | Molecular Weight | ESI-MS (M + H) |
|---|---|---|---|---|
| 25 | Chiral | $C_{25}H_{26}N_4O_3 \cdot CH_2O_2$ | 476.5302 | 430.2 |
| 26 | Chiral | $C_{25}H_{26}N_4O_3 \cdot CH_2O_2$ | 476.5302 | 430.2 |
| 27 | 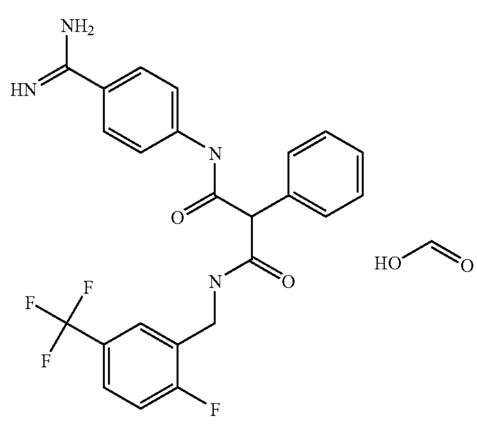 | $C_{24}H_{20}F_4N_4O_2 \cdot CH_2O_2$ | 518.4648 | 472.15 |

TABLE 1-continued

| Example No. | Structure | Empirical Formula | Molecular Weight | ESI-MS (M + H) |
|---|---|---|---|---|
| 28 | 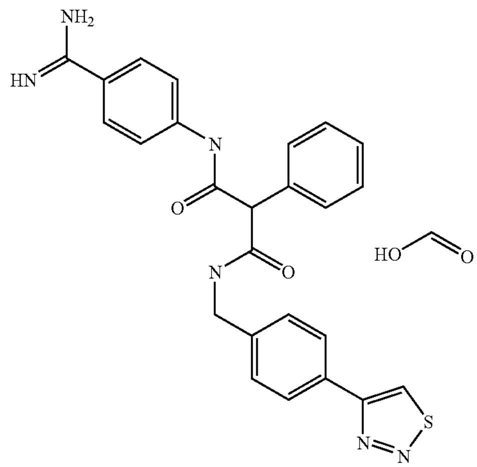 | $C_{25}H_{22}N_6O_2S \cdot CH_2O_2$ | 516.5796 | 470.15 |
| 29 | 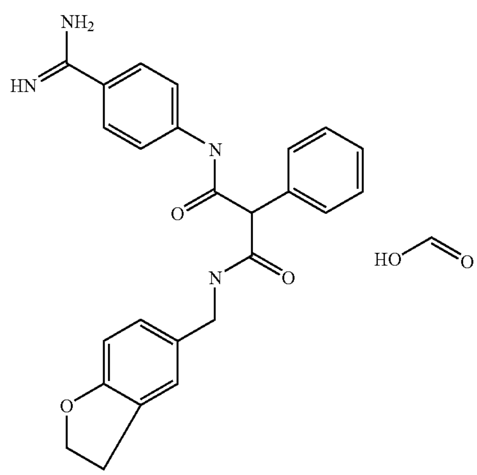 | $C_{25}H_{24}N_4O_3 \cdot CH_2O_2$ | 474.5144 | 428.18 |
| 30 | Chiral | $C_{26}H_{28}N_4O_3 \cdot CH_2O_2$ | 490.557 | 444.22 |

TABLE 1-continued

| Example No. | Structure | | Empirical Formula | Molecular Weight | ESI-MS (M + H) |
|---|---|---|---|---|---|
| 31 | 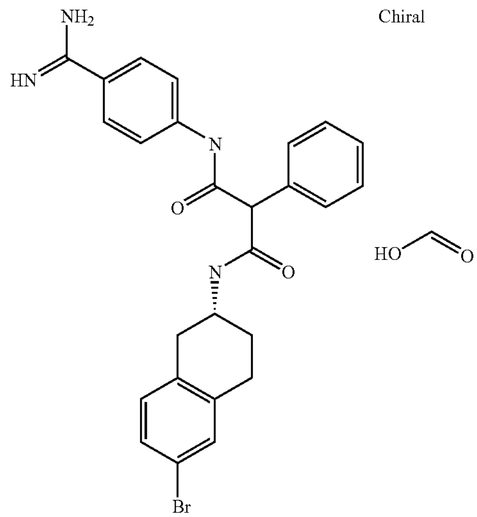 | Chiral | C₂₆H₂₅BrN₄O₂·CH₂O₂ | 551.4383 | 504.12 |
| 32 | 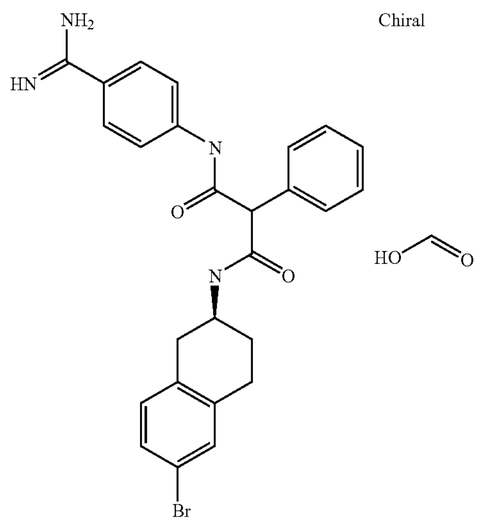 | Chiral | C₂₆H₂₅BrN₄O₂·CH₂O₂ | 551.4383 | 504.12 |
| 33 | 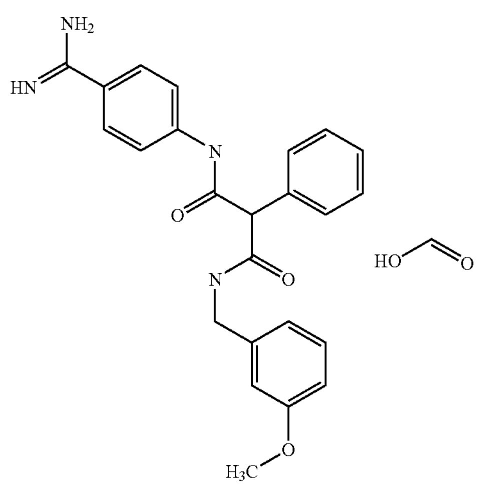 | | C₂₄H₂₄N₄O₃·CH₂O₂ | 462.5034 | 416.18 |

TABLE 1-continued
| Example No. | Structure | Empirical Formula | Molecular Weight | ESI-MS (M + H) |
|---|---|---|---|---|
| 34 | 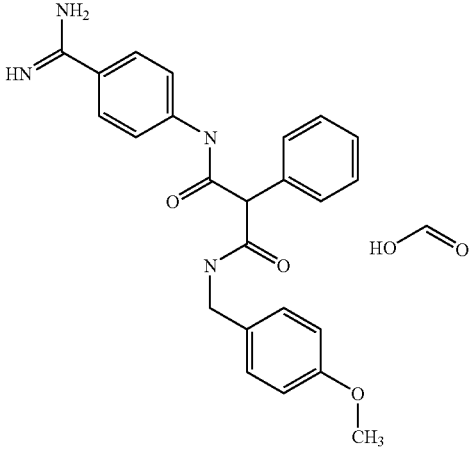 | $C_{24}H_{24}N_4O_3 \cdot CH_2O_2$ | 462.5034 | 416.18 |
| 35 | 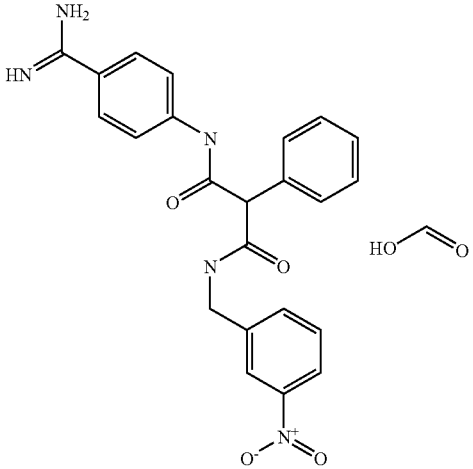 | $C_{23}H_{21}N_5O_4 \cdot CH_2O_2$ | 477.4747 | 431.16 |
| 36 | 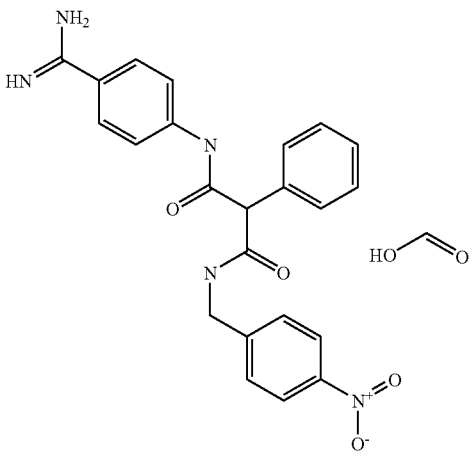 | $C_{23}H_{21}N_5O_4 \cdot CH_2O_2$ | 477.4747 | 431.16 |

TABLE 1-continued

| Example No. | Structure | Empirical Formula | Molecular Weight | ESI-MS (M + H) |
|---|---|---|---|---|
| 37 | 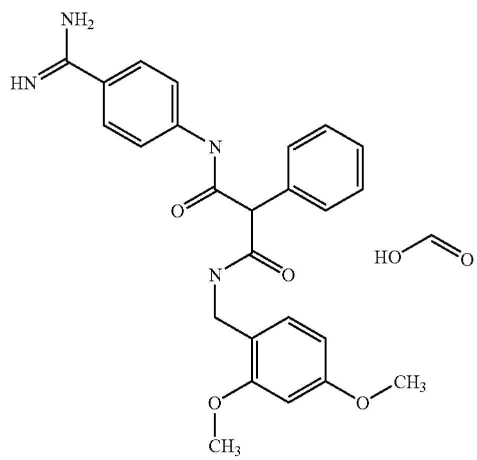 | $C_{25}H_{26}N_4O_4 \cdot CH_2O_2$ | 492.5292 | 446.2 |
| 38 | 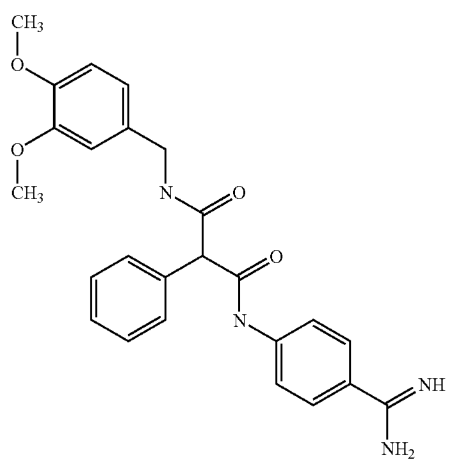 | $C_{25}H_{26}N_4O_4$ | 446.5044 | 447.15 |
| 39 | 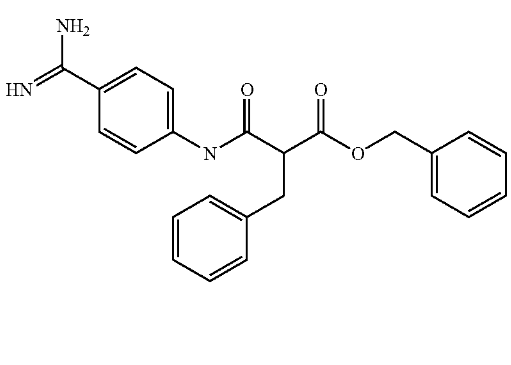 | $C_{24}H_{23}N_3O_3$ | 401.4637 | 402.1 |

TABLE 1-continued

| Example No. | Structure | Empirical Formula | Molecular Weight | ESI-MS (M + H) |
|---|---|---|---|---|
| 40 | 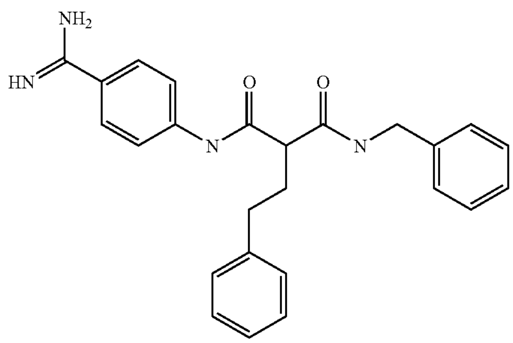 | $C_{25}H_{26}N_4O_2$ | 414.5064 | 415.2 |
| 41 | 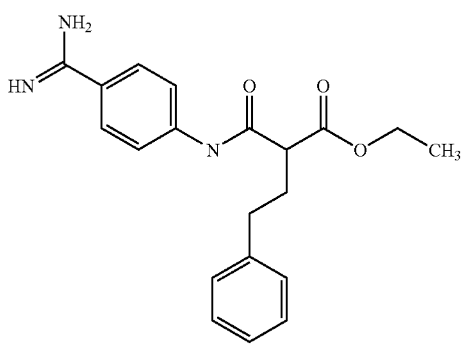 | $C_{20}H_{23}N_3O_3$ | 353.4197 | 354.1 |
| 42 | Chiral | $C_{30}H_{30}N_4O_2$ | 478.593 | 478.8 |
| 43 | Chiral | $C_{28}H_{26}N_4O_2 \cdot CH_2O_2$ | 496.5642 | 450.21 |

TABLE 1-continued
| Example No. | Structure | Empirical Formula | Molecular Weight | ESI-MS (M + H) |
|---|---|---|---|---|
| 44 | Chiral 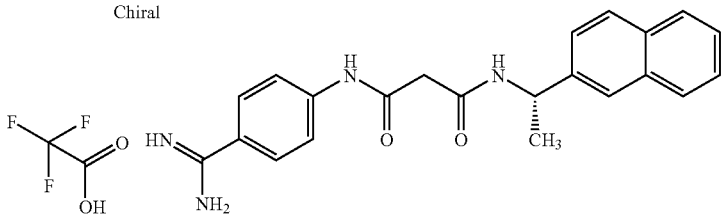 | $C_{22}H_{22}N_4O_2 \cdot C_2HF_3O_2$ | 488.46 | 375.20 |
| 45 | 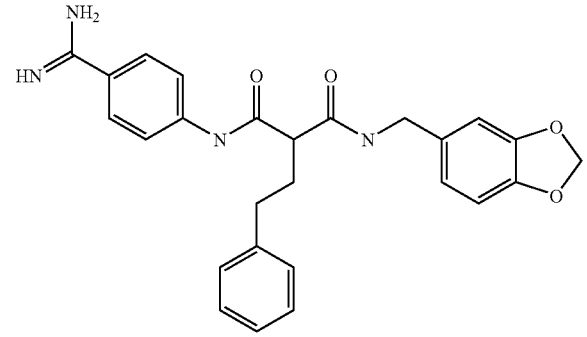 | $C_{26}H_{26}N_4O_4$ | 458.515 | 459.1 |
| 46 | 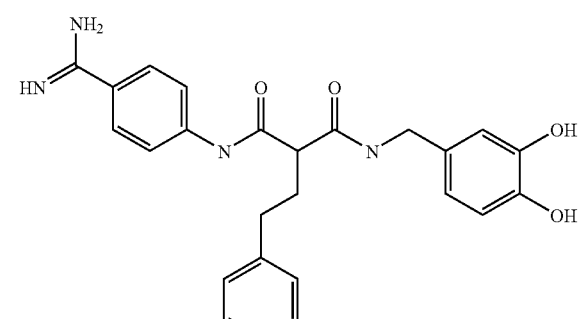 | $C_{25}H_{26}N_4O_4$ | 446.504 | 447.1 |

TABLE 1-continued
| Example No. | Structure | Empirical Formula | Molecular Weight | ESI-MS (M + H) |
|---|---|---|---|---|
| 47 | 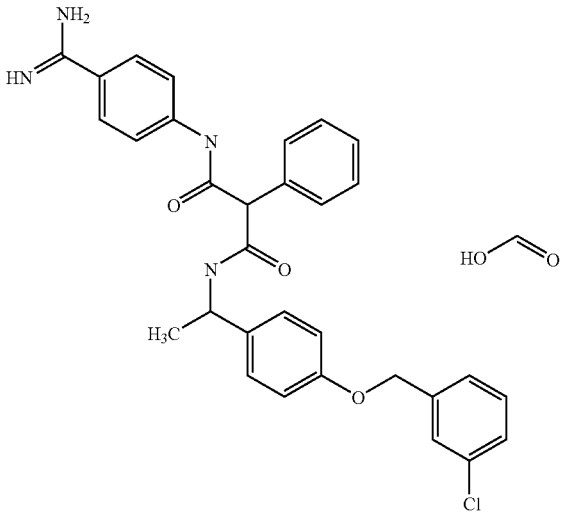 | C₃₁H₂₉ClN₄O₃·CH₂O₂ | 587.073 | 540.19 |
| 48 | 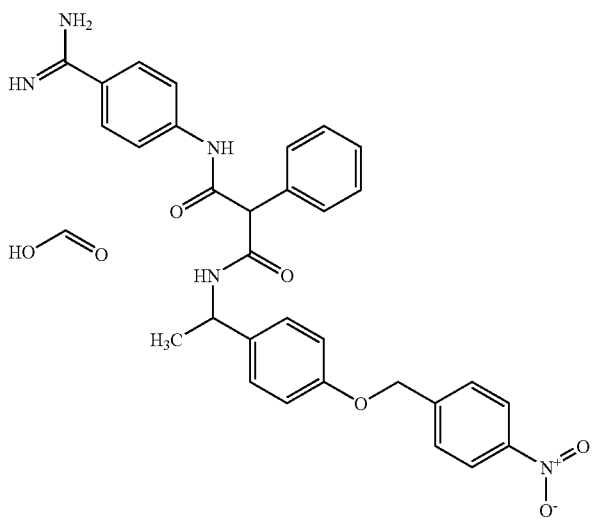 | C₃₁H₂₉N₅O₅·CH₂O₂ | 597.625 | 551.22 |

TABLE 1-continued

| Example No. | Structure | Empirical Formula | Molecular Weight | ESI-MS (M + H) |
|---|---|---|---|---|
| 49 | 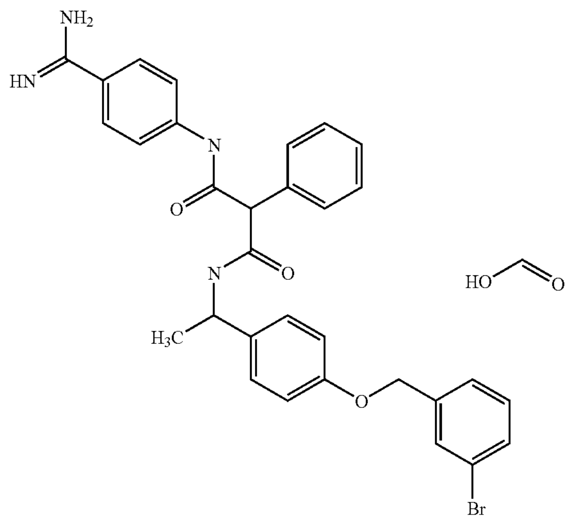 | $C_{31}H_{29}BrN_4O_3 \cdot CH_2O_2$ | 631.524 | 584.14 |
| 50 | 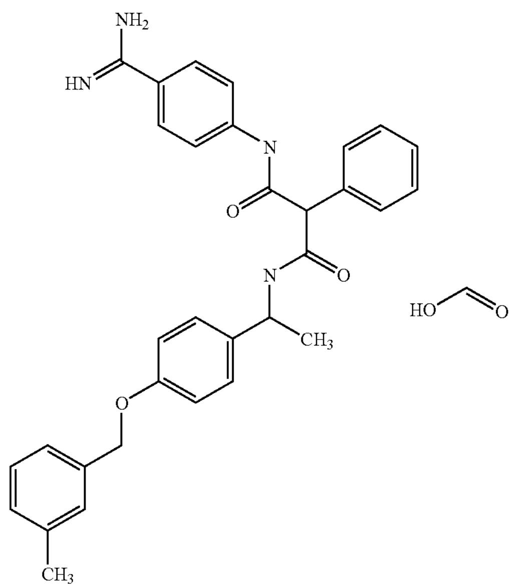 | $C_{32}H_{32}N_4O_3 \cdot CH_2O_2$ | 566.655 | 520.25 |
| 51 | 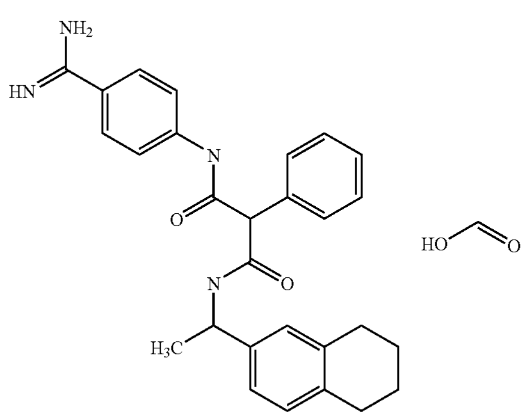 | $C_{28}H_{30}N_4O_2 \cdot CH_2O_2$ | 500.596 | 454.24 |

TABLE 1-continued

| Example No. | Structure | Empirical Formula | Molecular Weight | ESI-MS (M + H) |
|---|---|---|---|---|
| 52 | 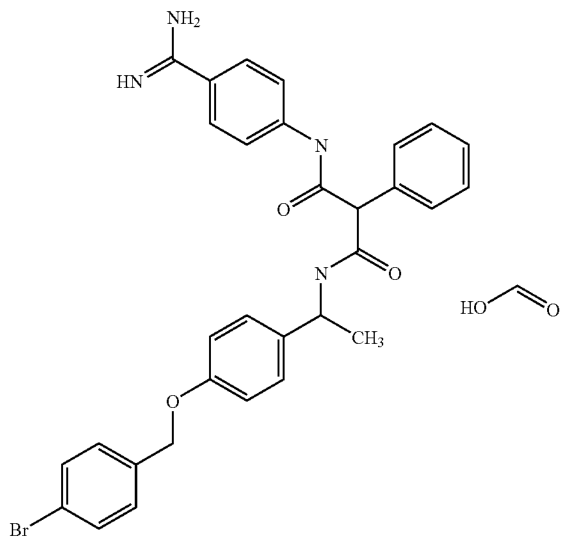 | $C_{31}H_{29}BrN_4O_3 \cdot CH_2O_2$ | 631.524 | 584.14 |
| 53 | 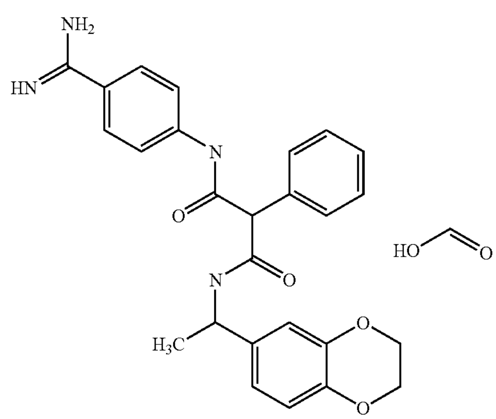 | $C_{26}H_{26}N_4O_4 \cdot CH_2O_2$ | 504.54 | 458.20 |
| 54 | 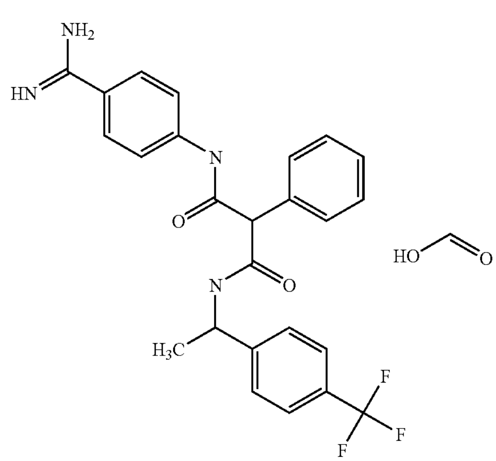 | $C_{25}H_{23}F_3N_4O_2 \cdot CH_2O_2$ | 514.502 | 514.51 |

TABLE 1-continued

| Example No. | Structure | Empirical Formula | Molecular Weight | ESI-MS (M + H) |
|---|---|---|---|---|
| 55 | 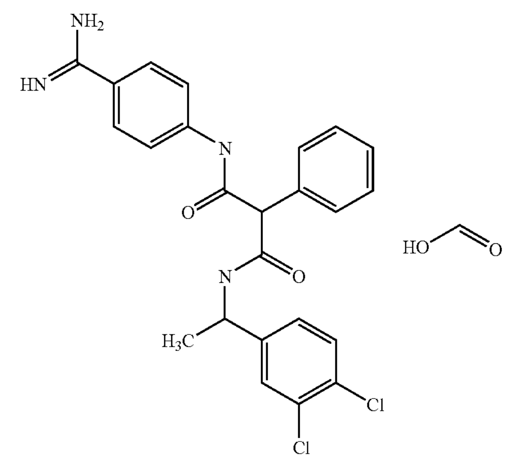 | $C_{24}H_{22}Cl_2N_4O_2 \cdot CH_2O_2$ | 515.395 | 468.11 |
| 56 | 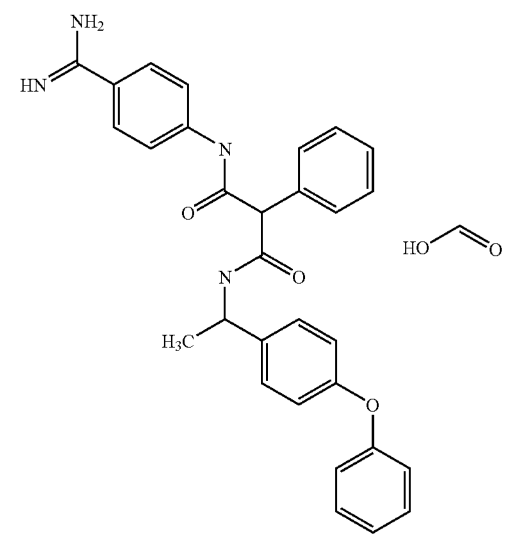 | $C_{30}H_{28}N_4O_3 \cdot CH_2O_2$ | 538.601 | 492.22 |
| 57 | 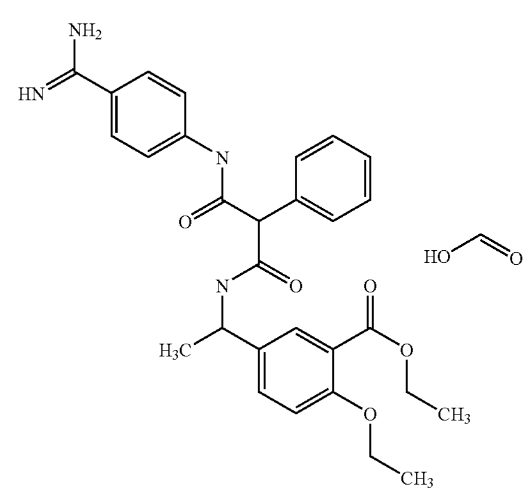 | $C_{29}H_{32}N_4O_5 \cdot CH_2O_2$ | 562.62 | 516.24 |

TABLE 1-continued

| Example No. | Structure | Empirical Formula | Molecular Weight | ESI-MS (M + H) |
|---|---|---|---|---|
| 58 | 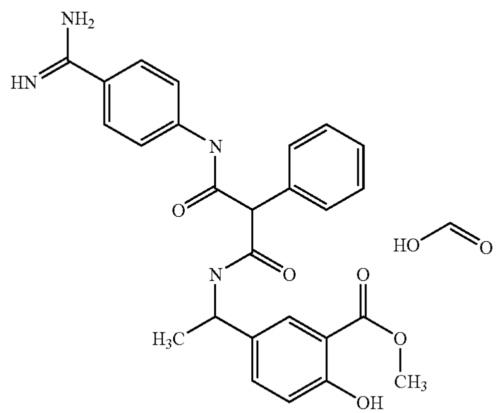 | $C_{26}H_{26}N_4O_5 \cdot CH_2O_2$ | 520.539 | 474.19 |
| 59 | 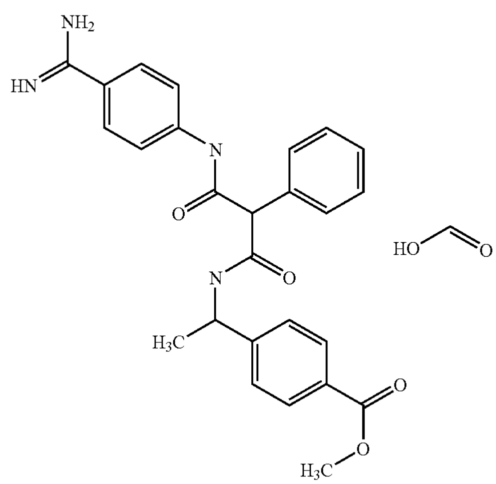 | $C_{26}H_{26}N_4O_4 \cdot CH_2O_2$ | 504.54 | 458.2 |
| 60 | 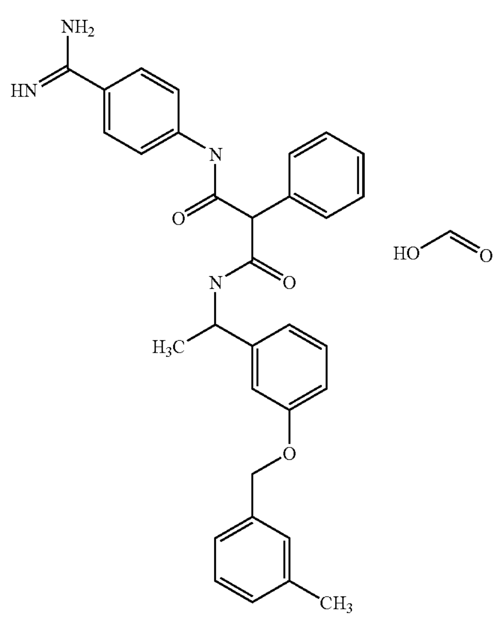 | $C_{32}H_{32}N_4O_3 \cdot CH_2O_2$ | 566.655 | 520.25 |

TABLE 1-continued

| Example No. | Structure | Empirical Formula | Molecular Weight | ESI-MS (M + H) |
| --- | --- | --- | --- | --- |
| 61 | 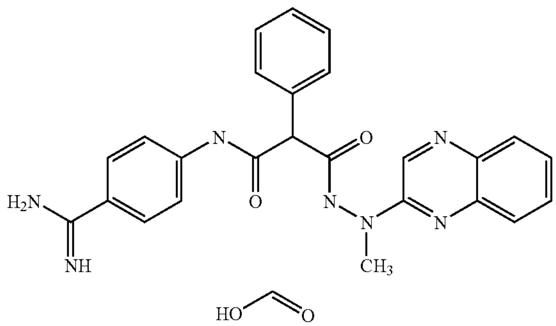 | C₂₅H₂₃N₇O₂·CH₂O₂ | 499.529 | 453.19 |
| 62 | 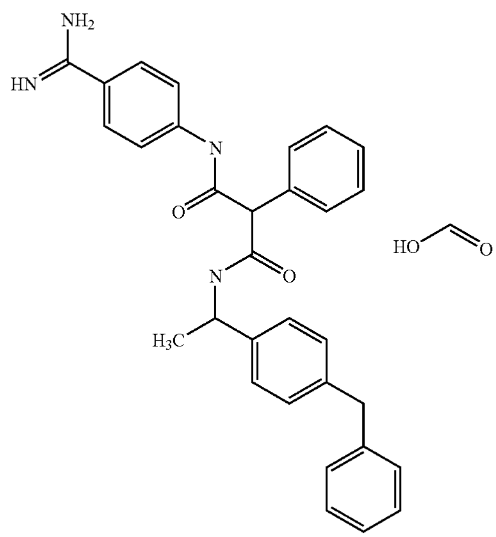 | C₃₁H₃₀N₄O₂·CH₂O₂ | 536.629 | 490.24 |
| 63 | 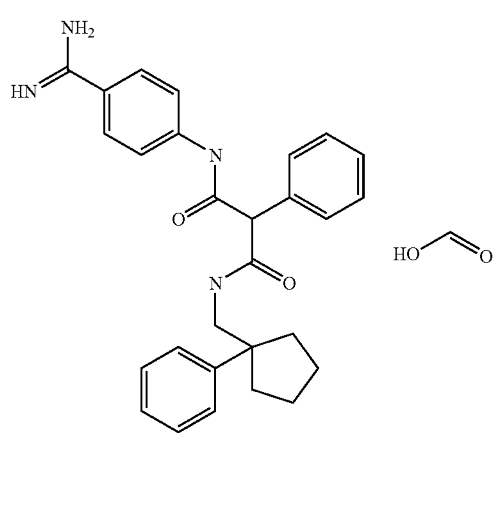 | C₂₈H₃₀N₄O₂·CH₂O₂ | 500.596 | 454.24 |

TABLE 1-continued
| Example No. | Structure | | Empirical Formula | Molecular Weight | ESI-MS (M + H) |
|---|---|---|---|---|---|
| 64 | 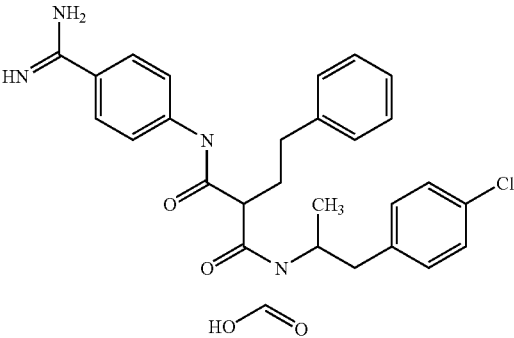 | | $C_{27}H_{29}ClN_4O_2 \cdot CH_2O_2$ | 523.03 | 477.0 |
| 65 | 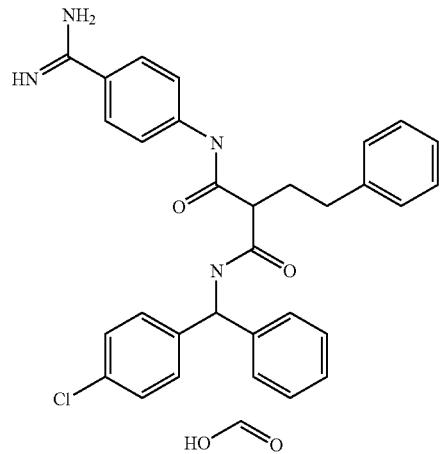 | | $C_{31}H_{29}ClN_4O_2 \cdot CH_2O_2$ | 571.074 | 525.0 |
| 66 | 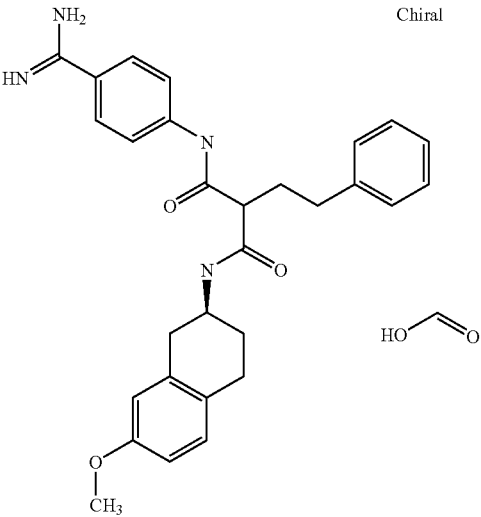 | Chiral | $C_{29}H_{32}N_4O_3 \cdot CH_2O_2$ | 530.622 | 485.0 |

TABLE 1-continued
| Example No. | Structure | Empirical Formula | Molecular Weight | ESI-MS (M + H) |
|---|---|---|---|---|
| 67 | 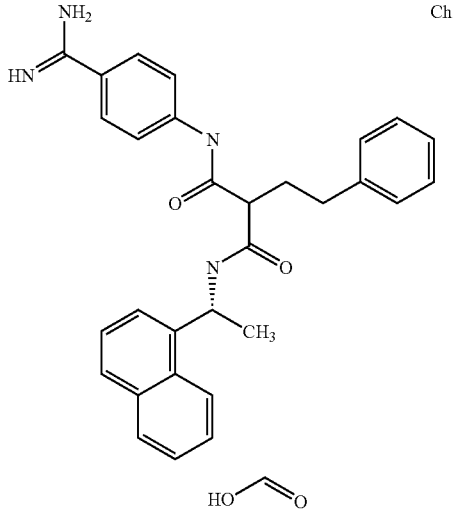 Chiral | C₃₀H₃₀N₄O₂·CH₂O₂ | 524.618 | 479.0 |
| 68 | 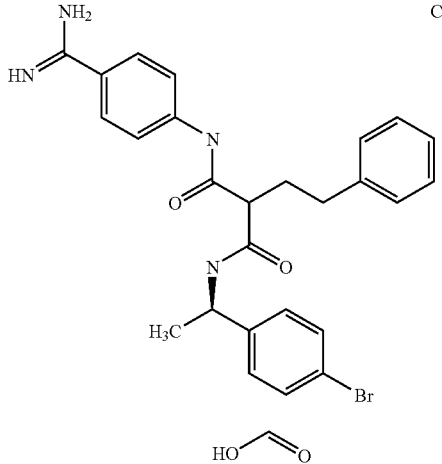 Chiral | C₂₆H₂₇BrN₄O₂CH₂O₂ | 553.454 | 506.9 |
| 69 | 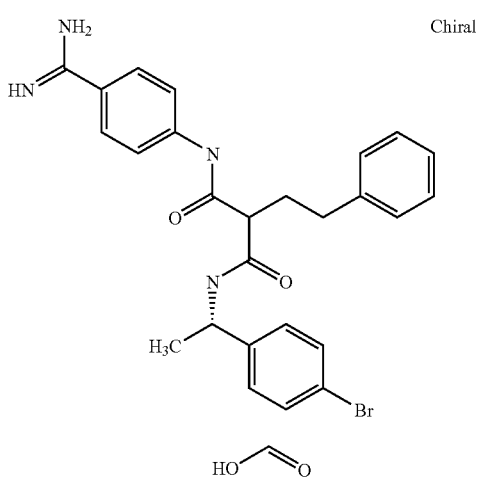 Chiral | C₂₆H₂₇BrN₄O₂CH₂O₂ | 553.454 | 506.9 |

TABLE 1-continued

| Example No. | Structure | Empirical Formula | Molecular Weight | ESI-MS (M + H) |
|---|---|---|---|---|
| 70 | Chiral | $C_{30}H_{30}N_4O_2 \cdot CH_2O_2$ | 524.618 | 479.0 |
| 71 | 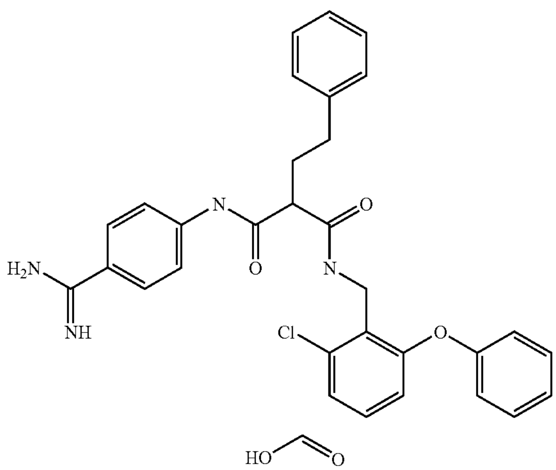 | $C_{31}H_{29}ClN_4O_3CH_2O_2$ | 587.073 | 541.0 |
| 72 | 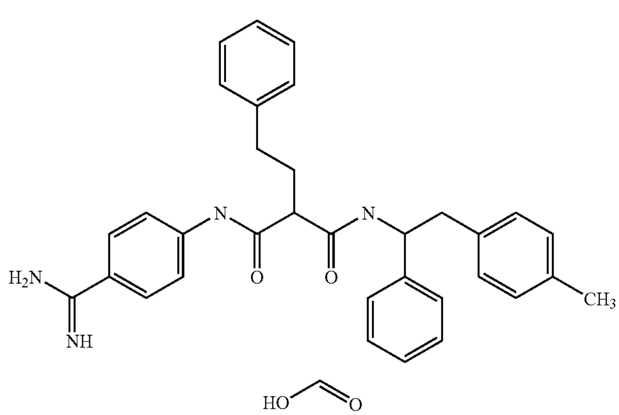 | $C_{33}H_{34}N_4O_2 \cdot CH_2O_2$ | 564.682 | 519.1 |

TABLE 1-continued

| Example No. | Structure | Empirical Formula | Molecular Weight | ESI-MS (M + H) |
|---|---|---|---|---|
| 73 | 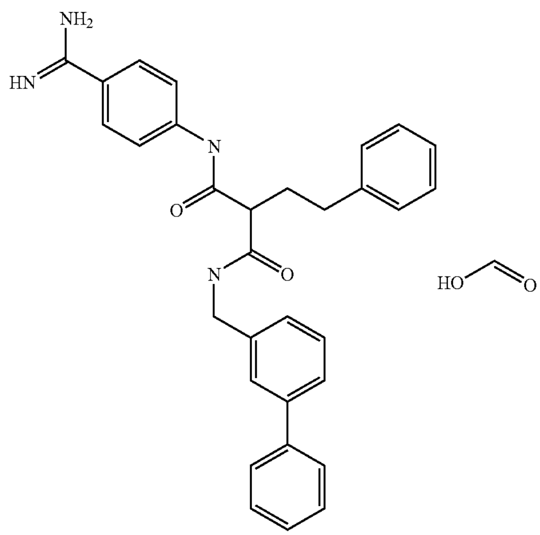 | $C_{31}H_{30}N_4O_2 \cdot CH_2O_2$ | 536.629 | 491.0 |
| 74 | 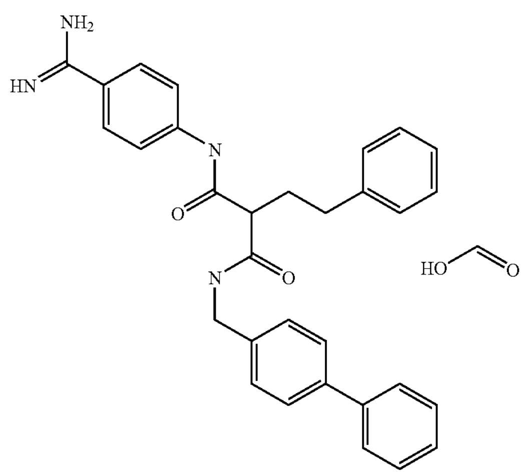 | $C_{31}H_{30}N_4O_2 \cdot CH_2O_2$ | 536.629 | 491.0 |
| 75 | 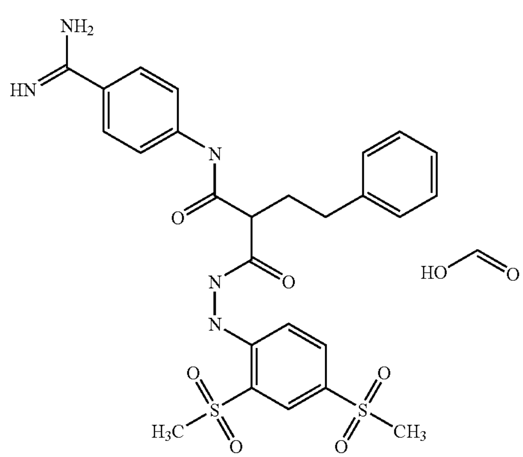 | $C_{26}H_{29}N_5O_6S_2 \cdot CH_2O_2$ | 617.701 | 571.9 |

TABLE 1-continued
| Example No. | Structure | Empirical Formula | Molecular Weight | ESI-MS (M + H) |
|---|---|---|---|---|
| 76 | 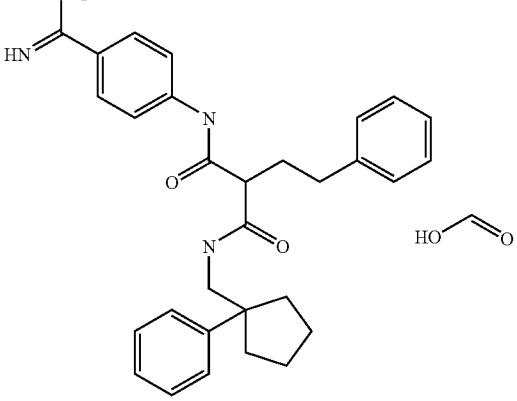 | $C_{30}H_{34}N_4O_2 \cdot CH_2O_2$ | 528.649 | 483.1 |
| 77 | 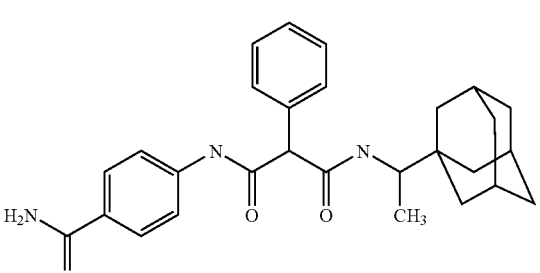 | $C_{28}H_{34}N_4O_2$ | 458.603 | 459.3 |
| 78 | 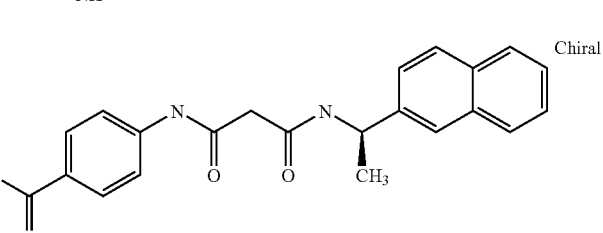 Chiral | $C_{22}H_{22}N_4O_2$ | 374.442 | 375.2 |
| 79 | ClH 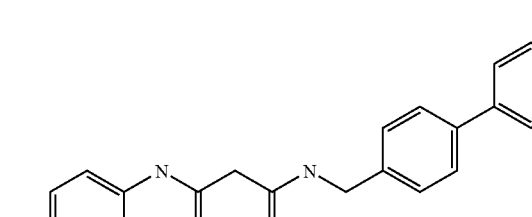 | $C_{23}H_{22}N_4O_2 \cdot ClH$ | 422.914 | 388.4 |
| 80 | ClH 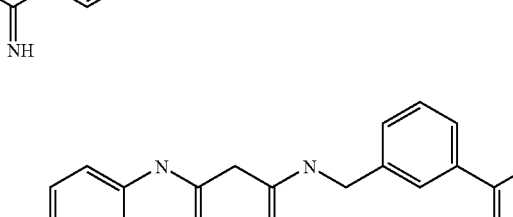 | $C_{23}H_{22}N_4O_2 \cdot ClH$ | 422.914 | 388.2 |

TABLE 1-continued

| Example No. | Structure | Empirical Formula | Molecular Weight | ESI-MS (M + H) |
|---|---|---|---|---|
| 81 | Chiral | $C_{28}H_{26}N_4O_2 \cdot CH_2O_2$ | 496.564 | 450.2 |
| 82 | Chiral | $C_{28}H_{26}N_4O_2 \cdot CH_2O_2$ | 496.564 | 450.2 |
| 83 | 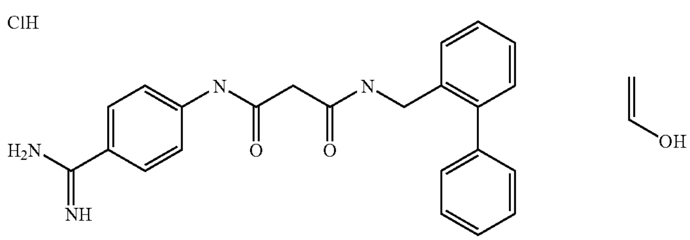 | $C_{23}H_{22}N_4O_2 \cdot ClH$ | 422.914 | 387.2 |
| 84 | 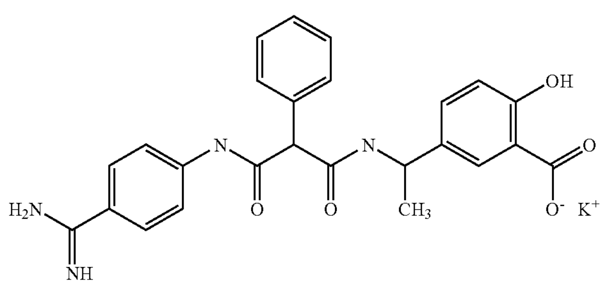 | $C_{25}H_{23}N_4O_5 \cdot K$ | 498.578 | 461.1 |
| 85 | 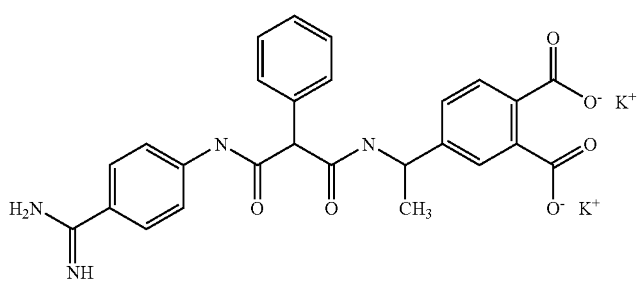 | $C_{26}H_{22}N_4O_6 \cdot 2K$ | 564.678 | 489.2 |

TABLE 1-continued

| Example No. | Structure | Empirical Formula | Molecular Weight | ESI-MS (M + H) |
|---|---|---|---|---|
| 86 | 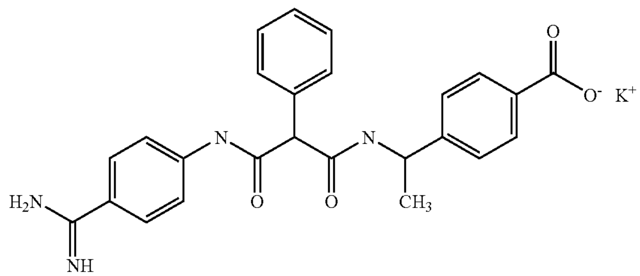 | $C_{25}H_{23}N_4O_4 \cdot K$ | 482.579 | 454.2 |
| 87 | Chiral | $C_{25}H_{26}N_4O_4$ | 446.504 | 447.3 |

Pharmacological Testing:

The ability of compounds of formula I to inhibit factor VIIa or other enzymes like factor Xa, thrombin, plasmin, or trypsin can be assessed by determining the concentration of the compound of formula I that inhibits enzyme activity by 50%, i.e., the $IC_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the $IC_{50}$ value is corrected for competition with substrate using the formula $Ki = IC_{50}/[1+(\text{substrate concentration}/Km)]$ wherein Km is the Michaelis-Menten constant (Chen and Prusoff, *Biochem. Pharmacol.* 22 (1973), 3099-3108; I. H. Segal, *Enzyme Kinetics,* 1975, John Wiley & Sons, New York, 100–125; which are incorporated herein by reference).

Factor VIIa (FVIIa) Assay:

The inhibitory activity (expressed as inhibition constant Ki (FVIIa)) of compounds of formula I towards factor VIIa/TF activity was determined using a chromogenic assay essentially as described previously (J. A. Ostrem et al., *Biochemistry* 37 (1998) 1053–1059, which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl$_2$, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration).

The following test results (inhibition constants Ki(FVIIa)) were obtained:

| Example Compound | Ki (FVIIa) (µM) | Example Compound | Ki (FVIIa) (µM) |
|---|---|---|---|
| 1 | 14 | 26 | 0.381 |
| 3 | 0.198 | 28 | 6.02 |
| 6 | 3.825 | 35 | 3.005 |
| 8 | 7.116 | 38 | 17.35 |
| 12 | 0.301 | 40 | 2.81 |
| 17 | 6.615 | 42 | 17.061 |
| 20 | 5.134 | 43 | 0.124 |
| 23 | 0.157 | 44 | 0.376 |

What is claimed is:

1. A compound of formula I,

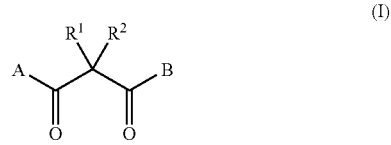

wherein:

A is a derivative of formula II,

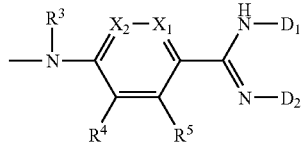

(II)

wherein:
R³ is hydrogen, —OH, or —(C₁–C₇)-alkyl;
R⁴ and R⁵, independently of one another, are
1. hydrogen;
2. —(C₁–C₇)-alkyl;
3. —OH;
4. —O—(C₁–C₇)-alkyl;
5. halogen;
6. —NH₂; or
7. —NO₂;
One of X₁ and X₂ is a nitrogen and the other a carbon substituted by R⁴ wherein R⁴ is as defined above;
D₁ and D₂, independently of one another, are
1. hydrogen;
2. —C(O)—(C₁–C₇)-alkyl;
3. —C(O)-aryl;
4. —C(O)—(C₁–C₇)-alkyl-aryl;
5. —C(O)—O—(C₁–C₇)-alkyl;
6. —C(O)—O—(C₁–C₇-)-alkyl-aryl; or
7. —C(O)—O—(C₁–C₆)-aryl; or
D₁ is hydrogen, when D₂ is
1. —OH;
2. —O—C(O)—(C₁–C₇)-alkyl;
3. —O—C(O)-aryl; or
4. —O—C(O)—(C₁–C₇)-alkyl-aryl; or
D₁ and D₂, together with the nitrogen to which they are attached, form a cycle of the formula VIII

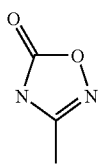

(VIII)

R¹ is 1. hydrogen;
2. —(C₁–C₇)-alkyl;
3. —OH;
4. —O—(C₁–C₇)-alkyl; or
5. —N—(R⁶)₂, wherein R⁶ is, independently of one another, hydrogen, —C(O)-aryl, —C(O)—(C₁–C₇)-alkyl-aryl, —C(O)—(C₁–C₇)-alkyl, —(C₁–C₇)-alkyl, —C(O)—N(H)-aryl, —C(O)—N(H)—(C₁–C₇)-alkyl-aryl, —(C₁–C₆)—N(H)-alkyl, —C(O)—O-aryl, —C(O)—O—(C₁–C₇)-alkyl-aryl, —C(O)—O—(C₁–C₇)-alkyl-, S(O₂)-aryl, or —S(O₂)—(C₁–C₇)-alkyl;
R² is 1. aryl, wherein aryl is unsubstituted or mono- to tri-substituted, independently of one another, by
1.1 —CF₃;
1.2. halogen;
1.3 —OH;
1.4 —CN;
1.5 sulfo;
1.6 —NO₂;
1.7 —NH₂;
1.8 —O—(C₁–C₇)-alkyl;
1.9 substituted amino;
1.10 —COOH;
1.11 —(C₁–C₇)-alkyl;
1.12 carbamyl;
1.13 carbonyl;
1.14 alkoxycarbonyl;
1.15 methylendioxyl;
1.16 aryloxy, wherein aryloxy is unsubstituted or mono- to tri-substituted, independently of one another, by a substituent as defined by 1.1 to 1.15;
1.17 —O—(C₁–C₇)-alkyl-aryl, wherein aryl is unsubstituted or mono- to tri-substituted, independently of one another, by a substituent as defined by 1.1 to 1.15;
1.18 Het-group, wherein Het-group is unsubstituted or mono- to tri-substituted, independently of one another, by a substituent as defined by 1.1 to 1.15; or
1.19 —(C₀–C₄)-alkyl-aryl, wherein aryl is unsubstituted or mono- to tri-substituted, independently of one another, by a substituent as defined by 1.1 to 1.15;
2. hydrogen;
3. Het-group, wherein the Het-group is unsubstituted or mono- to tri-substituted, independently of one another, by a substituent as defined by 1.1 to 1.19 above;
4. —(CH₂)ₘ—Yₙ—(CH₂)ₒ-aryl, in which
m, n, and o are, independently of one another, 0, 1, or 2, provided that at least one of m, n, and o is not 0;
aryl is unsubstituted or mono- to tri-substituted, independently of one another, by a substituent as defined by 1.1 to 1.19 above; and
Y is —O—, —S—, or —N—(R⁶) wherein R⁶ is hydrogen or —(C₁–C₇)-alkyl, provided n is 1, or Y is —N(R⁶)—N(R⁶)— wherein R⁶ is, independently of one another, hydrogen or —(C₁–C₇)-alkyl, or —N=N—, provided n is 2; or
5. —(CH₂)ₘ—Yₙ—(CH₂)ₒ-Het-group, in which m, n, and o are, independently of one another, 0, 1, or 2, provided that at least one of m, n, and o is not 0;
Het-group is unsubstituted or mono- to tri-substituted, independently of one another, by a substituent as defined by 1.1 to 1.19 above; and
Y is as defined above; or
R¹ and R², together with the carbon to which they are bonded, form
1. a —(C₃–C₇)-cycloalkyl, wherein cycloalkyl is unsubstituted or mono- to tri-substituted, independently of one another, by a substituent as defined by 1.1 to 1.19 above;
2. a —(C₃–C₇)-cycloalkyl, wherein cycloalkyl is unsubstituted or mono- to disubstituted, independently of one another, and fused to an aryl- or Het-group-ring, which itself is unsubstituted or mono- to tri-substituted, independently of one another, by a substituent as defined by 1.1 to 1.19 above;
3. a Het-group, wherein the Het-group is unsubstituted or mono- to tri-substituted, independently of one another, by a substituent as defined by 1.1 to 1.19 above; or
4. a keto-group, which may partially or totally exist in a hydrated state; provided that, when R¹ is as defined above under 3, 4, or 5, then R² is not directly bonded to formula I via a oxygen-, sulfur- or nitrogen-;

B is 1. —N(R$^7$)—(CH—(R$^8$))$_p$-aryl, in which
  aryl is unsubstituted or mono- to tri-substituted, independently of one another, by a substituent as defined by 1.1 to 1.19 above;
  p is 0, 1, or 2;
  R$^7$ is 1.1 hydrogen;
    1.2 —(C$_1$–C$_7$)-alkyl;
    1.3 —OH; or
    1.4 —N—(R$^6$)$_2$, wherein R$^6$ is, independently of one another, hydrogen or —(C$_1$–C$_7$)-alkyl;
  R$^8$ is 1.1 hydrogen;
    1.2 —(C$_1$–C$_7$)-alkyl;
    1.3 —(C$_2$–C$_7$)-alkenyl;
    1.4 —(C$_2$–C$_7$)-alkynyl;
    1.5 —(C$_0$–C$_3$)-alkyl-(C$_3$–C$_7$)-cycloalkyl;
    1.6 —CN;
    1.7 aryl, aryl is unsubstituted or mono- or di-substituted, independently of one another, by a substituent as defined by 1.1 to 1.19 above;
    1.8 a Het-group, wherein the Het-group is unsubstituted or mono- or di-substituted, independently of one another, by a substituent as defined by 1.1 to 1.19 above;
    1.9 —(CH—(R$^8$))— forms a —(C$_3$–C$_7$)-cycloalkyl derivative; or
    1.10 —(C$_0$–C$_4$)-alkyl-O—(C$_1$–C$_7$)-alkyl;
2. —O—(CH—(R$^8$))$_p$-aryl, wherein aryl, R$^8$, and p are as defined above;
3. —N(R$^7$)—(CH—(R$^8$))$_p$-Het-group, wherein the Het-group is unsubstituted or mono- or di-substituted, independently of one another, by a substituent as defined by 1.1 to 1.19 above, and R$^7$, R$^8$, and p are as defined above;
4. —N(R$^9$)—N(R$^{9'}$)—(CH—(R$^8$))$_q$-aryl, in which
  aryl is unsubstituted or mono- to tri-substituted, independently of one another, by a substituent as defined by 1.1 to 1.9 above;
  q is 0, 1, or 2;
  R$^9$ and R$^{9'}$ are, independently of one another, hydrogen, —(C$_1$–C$_7$)-alkyl, or —(C$_1$–C$_3$)-alkyl-aryl; and
  R$^8$ is as defined above;
5. —O—N(R$^9$)—(CH—(R$^8$))$_q$-aryl, in which
  aryl is unsubstituted or mono- to tri-substituted, independently of one another, by a substituent as defined by 1.1 to 1.19 above;
  q is 0, 1, or 2; and
  R$^8$ and R$^9$ are as defined above;
6. —N(R$^9$)—N(R$^{9'}$)—(CH—(R$^8$))$_q$-Het-group, in which
  Het-group is unsubstituted or mono- to tri-substituted, independently of one another, by a substituent as defined by 1.1 to 1.19 above;
  q is 0, 1, or 2; and
  R$^8$, R$^{9'}$, and R$^9$ are as defined above; or
7. —O—N(R$^9$)—(CH—(R$^8$))$_q$-Het-group, in which
  Het-group is unsubstituted or mono- to tri-substituted, independently of one another, by a substituent as defined by 1.1 to 1.19 above;
  q is 0, 1, or 2; and
  R$^8$ and R$^9$ are as defined above;
in any stereoisomeric form or mixture thereof in any ratio, or a physiologically tolerable salt thereof.

2. A compound of claim 1, wherein
A is a derivative of formula II, wherein
  R$^3$ is hydrogen;
  R$^4$ and R$^5$, independently of one another, are hydrogen or halogen; and X$_1$ and X$_2$, independently of one another, are carbon or nitrogen;
R$^1$ is hydrogen or —(C$_1$–C$_2$)-alkyl;
R$^2$ is hydrogen, phenyl, or —(C$_1$–C$_2$)-alkyl-phenyl;
B is 1. —N(R$^7$)—(CH—(R$^8$))$_p$-aryl, in which
  aryl is indanyl, phenyl, tetralinyl, naphthalinyl, which are unsubstituted or mono- to disubstituted, independently of one another, by
    1.1 Br, Cl, or F;
    1.2 —CF$_3$;
    1.3 —NO$_2$;
    1.4 methylendioxyl;
    1.5 —OH;
    1.6 phenyl;
    1.7 phenoxy;
    1.8 benzyloxy;
    1.9 —O—(C$_1$–C$_7$)-alkyl-phenyl, wherein phenyl is unsubstituted or or mono- to tri-substituted, independently of one another, by
      1.9.1 Br, Cl, or F;
      1.9.2 —(C$_1$–C$_4$)-alkyl; or
      1.9.3 —NO$_2$;
    1.10 —C(O)—O—(C$_1$–C$_4$)-alkyl;
    1.11 —O—(C$_1$–C$_4$)-alkyl;
    1.12 —SO$_2$—(C$_1$–C$_4$)-alkyl;
    1.13 —COOH;
    1.14 —(C$_1$–C$_3$)-alkyl; or
    1.15 methoxyl;
  p is 0, 1, or 2;
  R$^7$ is hydrogen;
  R$^8$ is 1.1 hydrogen;
    1.2 —(C$_1$–C$_2$)-alkyl;
    1.3 —CN;
    1.4 phenyl, wherein phenyl is unsubstituted or mono- or di-substituted, independently of one another, by methoxy or halogen;
    1.5 —(C$_0$–C$_2$)-alkyl-O—(C$_1$–C$_4$)-alkyl;
    1.6 —(CH—(R$^8$))— forms a —(C$_4$–C$_6$)-cycloalkyl derivative;
    1.7 cyclopropylmethyl; or
    1.8 ethynyl;
2. —O—(CH—(R$^8$))$_p$-phenyl, wherein phenyl, R$^8$, and p are as defined above;
3. —N(R$^9$)—N(R$^{9'}$)—(CH—(R$^8$))$_q$-Het-group, in which
Het-group is quinoxaline, imidazolyl, benzimidazolyl, oxazolyl, benzoxazolyl, thiazolyl, indazolyl, benzothiazolyl, indolyl, indolinyl, or pyridinyl, wherein
Het-group is unsubstituted or mono- to di-substituted, independently of one another, by
    1.1 Br, Cl, or F;
    1.2 —CF$_3$;
    1.3 —NO$_2$;
    1.4 methylendioxyl;
    1.5 —OH;
    1.6 phenyl;
    1.7 phenoxy;
    1.8 benzyloxy;
    1.9 —O—(C$_1$–C$_7$)-alkyl-phenyl, wherein phenyl is unsubstituted or or mono- to tri-substituted, independently of one another, by
      1.9.1 Br, Cl, or F;
      1.9.2 —(C$_1$–C$_4$)-alkyl; or
      1.9.3 —NO$_2$;
    1.10 —C(O)—O—(C$_1$–C$_4$)-alkyl;
    1.11 —O—(C$_1$–C$_4$)-alkyl;
    1.12 —SO$_2$—(C$_1$–C$_4$)-alkyl;

1.13 —COOH;
1.14 —($C_1$–$C_3$)-alkyl; or
1.15 methoxyl;

$R^9$ and $R^{9'}$ are, independently of one another, hydrogen or —($C_1$–$C_2$)-alkyl;

$R^8$ is 1.1 hydrogen;
1.2 —($C_1$–$C_2$)-alkyl;
1.3 —CN;
1.4 phenyl, wherein phenyl is unsubstituted or mono- or di-substituted, independently of one another, by methoxy or halogen;
1.5 —($C_0$–$C_2$)-alkyl-O—($C_1$–$C_4$)-alkyl;
1.6 —(CH—($R^8$))— forms a —($C_4$–$C_6$)-cycloalkyl derivative;
1.7 cyclopropylmethyl; or
1.8 ethynyl; and q is 0, 1, or 2; or 4. —N($R_2^7$)—(CH—($R^8$))$_p$-Het-group$^2$, wherein the Het-group$^2$ is imidazolyl, benzimidazolyl, oxazolyl, benzoxazolyl, thiazolyl, benzothiazolyl, indolyl, indazolyl, indolinyl, or pyridinyl, wherein Het-group$^2$ is unsubstituted or mono-substituted by Br, Cl, F, —$CF_3$, —$NO_2$, phenyl, phenoxy, methyl, benzyloxy, or methoxy;

p is 0, 1, or 2;
$R^7$ is hydrogen;
$R^8$ is 1.1 hydrogen;
1.2 —($C_1$–$C_2$)-alkyl;
1.3 —CN;
1.4 phenyl, wherein phenyl is unsubstituted or mono- or di-substituted, independently of one another, by methoxy or halogen;
1.5 —($C_0$–$C_2$)-alkyl-O—($C_1$–$C_4$)-alkyl;
1.6 —(CH—($R^8$))— forms a —($C_4$–$C_6$)-cycloalkyl derivative;
1.7 cyclopropylmethyl; or
1.8 ethynyl.

3. A process for the preparation of a compound of claim 1, comprising linking the building blocks of formulae III, IV, and V

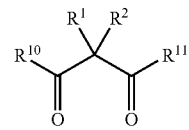

(III)

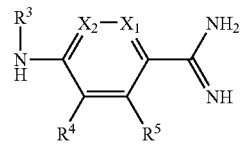

(IV)

HB (V)

wherein $R^{10}$ and $R^{11}$ are, independently of one another, a —OH group, an acid chloride, an ester or an activated ester, or a mixed anhydride, or any other activated species resulting from the reaction of the carboxylic acid with coupling reagents, and $R^1$, $R^2$, $R^3$, $R^4$, $R^5$, $R^7$, $R^8$, $X_1$, $X_2$, B, p, and aryl are as defined for formula I, by means of forming in a manner known per se an amide bond between the carboxylic acid derivative depicted in formula III and the —$NHR^3$ group depicted in formula IV and an amide bond or ester bond between the carboxylic acid derivative depicted in formula III and the —OH— or —NH— group depicted in formula V.

4. A pharmaceutical preparation, comprising one or more compounds of claim 1 and a pharmaceutically acceptable carrier.

5. A method for inhibiting or reducing blood clotting, comprising administering to a patient in need thereof an effective amount of one or more compounds of claim 1.

6. A method for treating restenoses, comprising administering to a patient in need thereof an effective amount of one or more compounds of claim 1.

* * * * *